United States Patent
Jang et al.

(10) Patent No.: US 11,814,690 B2
(45) Date of Patent: Nov. 14, 2023

(54) PROBE FOR DETECTING HEPATITIS B VIRUS AND USE THEREOF

(71) Applicant: THE CATHOLIC UNIVERSITY OF KOREA INDUSTRY—ACADEMIC COOPERATION FOUNDATION, Seoul (KR)

(72) Inventors: Jeong Won Jang, Seoul (KR); Hye Seon Kim, Seoul (KR); Jin Seoub Kim, Seoul (KR); Eung Ryoung Lee, Seoul (KR)

(73) Assignee: THE CATHOLIC UNIVERSITY OF KOREA INDUSTRY-ACADEMIC COOPERATION FOUNDATION, Seoul (KR)

( * ) Notice: Subject to any disclaimer, the term of this patent is extended or adjusted under 35 U.S.C. 154(b) by 326 days.

(21) Appl. No.: 17/089,432

(22) Filed: Nov. 4, 2020

(65) Prior Publication Data

US 2021/0130916 A1    May 6, 2021

(30) Foreign Application Priority Data

Nov. 4, 2019  (KR) .......................... 10-2019-0139264

(51) Int. Cl.
*C12Q 1/70* (2006.01)
*C12Q 1/6874* (2018.01)

(52) U.S. Cl.
CPC ........... *C12Q 1/706* (2013.01); *C12Q 1/6874* (2013.01)

(58) Field of Classification Search
CPC .............................. C12Q 1/706; C12Q 1/6874
USPC .............................................................. 506/2
See application file for complete search history.

(56) References Cited

U.S. PATENT DOCUMENTS 10,597,736 B2 *  3/2020  Storch .................... C12Q 1/701
2018/0223380 A1 *  8/2018  Lin ........................ C12Q 1/706

FOREIGN PATENT DOCUMENTS

| KR | 10-2013-0113046 | 10/2013 |
| KR | 10-2014-0022971 | 4/2015 |

OTHER PUBLICATIONS

Choi et. al. Hepatitis B virus from South Korea, complete genome. GenBank: DQ683578.1. Department of Internal Medicine, Yonsei University College of Medicine. 2006. [retrieved on Jan. 26, 2023]. Retrieved from the Internet <URL: https://www.ncbi.nlm.nih.gov/nuccore/DQ683578.1> (Year: 2006).*

(Continued)

*Primary Examiner* — Aaron A Priest
*Assistant Examiner* — Randi Lynn Beil
(74) *Attorney, Agent, or Firm* — NORTON ROSE FULBRIGHT US LLP

(57) ABSTRACT

A probe for detecting hepatitis B virus and a method for detecting an insertion site of hepatitis B virus at high efficiency based on the analysis method of next-generation sequencing using the probe is disclosed. A probe can be provided that is capable of confirming the insertion site of HBV in the human genome with a possibility of developing into liver cancer. In addition, by applying the probe to the analysis method of next-generation sequencing, HBV insertion sites in the human genome can be analyzed at low cost and high efficiency.

10 Claims, 5 Drawing Sheets
Specification includes a Sequence Listing.

(56) References Cited

OTHER PUBLICATIONS

Haslam et. al. Optimal probe length varies for targets with high sequence variation: Implications for probe library design for resequencing highly variable genes. Plos ONE. 3(6), 2008, 1-10. [retrieved on Jan. 31, 2023]. Retrieved from the Internet <DOI: 10.1371/journal.pone.0002500> (Year: 2008).*

Weiner et. al. Kits and their unique role in molecular biology: a brief retrospective. BioTechniques. 44, 2008, 701-704. (Year: 2008).*

Jang et al., "Detection of HBV Integration in the Human Genome Using High-Throughput Targeted Sequencing", Division of Hepatology, Department of Internal Medicine, The Catholic University of Korea, 2019.

Jang, "Detection of HBV Integration in the Human Genome Using High-Throughput Targeted Sequencing", Free Paper Session, The Catholic University of Korea, Jun. 21, 2019.

Jang et al, "Detection of HBV Integration in the Human Genome Using High-Throughput Targeted Sequencing", Department of Internal Medicine, The Catholic University of Korea Liver Research Center, 2019.

Yang, L. et al., "Molecular Characterization of HBV DNA Integration in Patients with Hepatitis and Hepatocellular Carcinoma", *Journal of Cancer*, 9(18), pp. 3225-3235, 2018.

\* cited by examiner

HBV breakpoints across the human chromosome -
- HBV breakpoints in the human genome, circos plot -

SEQUENCE LISTING

```
<160> NUMBER OF SEQ ID NOS: 215

<210> SEQ ID NO 1
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 1
ctccacaaca ttccaccaag ctctgctaga tcccagagtg aggggcctat attttcctgc      60
tggtggctcc agttccggaa cagtaaaccc tgttccgact attgtctcac ccatatcgtc     120

<210> SEQ ID NO 2
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 2
aagcaggcct tcactttctc gccaacttac aaggcctttc tgtgtaaaca atatctgcac      60
ctttaccccg ttgcccggca acggtcaggt ctctgccaag tatttgctga cgcaaccccc     120

<210> SEQ ID NO 3
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 3
ttcctcacat tcatttacag gaggacatta ttaatagatg tgaacaatat gtgggccctc      60
ttacagttaa tgaaaaaagg agattaaaat taattatgcc tgctaggttc tatcctaacc     120

<210> SEQ ID NO 4
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 4
ttaccaaata tttgccattg gacaaaggca ttaaaccata ttatcctgaa catgcagtta      60
atcattactt caaaactagg cattatttac atactctgtg gaaggcgggc attctatata     120
```

<210> SEQ ID NO 5
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 5
agagagaaac tacacgcagt gcctcattct gtgggtcacc atattcttgg gaacaagagc    60
tacagcatgg gaggttggtc ttccaaacct cgacaaggca tggggacgaa tctttctgtt   120

<210> SEQ ID NO 6
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 6
cccaatcctc tgggattctt tcccgatcac cagttggacc ctgcattcgg agccaactca    60
aacaatccag attgggactt caaccccaac aaggatcatt ggccagaggc aaatcaggta   120

<210> SEQ ID NO 7
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 7
ggagcgggag cattcgggcc agggttcacc ccaccacacg gcggtctttt ggggtggagc    60
ccgcaggctc agggcatatt gacaaccgtg ccagtagcac ctcctcctgc ctccaccaat   120

<210> SEQ ID NO 8
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 8
ctccaccaca ttccaccaag ctctactaga tcccagagtg aggggcctat attttcctgc    60
tggtggctcc agttccggaa cagtaaaccc tgttccgact actgcctcac ccatatcgtc   120

<210> SEQ ID NO 9
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 9
aatcttctcg aggactgggg accctgcacc gaacatggag agcacaacat caggattcct    60
aggacccctg ctcgtgttac aggcggggtt tttcttgttg acaagaatcc tcacaatacc   120

<210> SEQ ID NO 10
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 10

```
acagagtcta gactcgtggt ggacttctct caattttcta gggggagcac ccacgtgtcc    60
tggccaaaat tcgcagtccc caacctccaa tcactcacca acctcttgtc ctccaatttg   120
```

<210> SEQ ID NO 11
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 11

```
tcctggctat cgctggatgt gtctgcggcg ttttatcata ttcctcttca tcctgctgct    60
atgcctcatc ttcttgttgg ttcttctgga ctaccaaggt atgttgcccg tttgtcctct   120
```

<210> SEQ ID NO 12
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 12

```
acttccagga acatcaacta ccagcacggg accatgcaag acctgcacga ttcctgctca    60
aggaacctct atgtttccct cttgttgctg tacaaaacct tcggacggaa attgcacttg   120
```

<210> SEQ ID NO 13
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 13

```
actggatggg gcttggccat aggccatcgg cgcatgcgtg gaacctttgt ggctcctctg    60
ccgatccata ctgcggaact cctagcagct tgttttgctc gcagccggtc tggagcgaaa   120
```

<210> SEQ ID NO 14
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 14

```
tattcccatc ccatcatcct gggctttcgc aaaattccta tgggagtggg cctcagtccg    60
tttctcctgg ctcaatttac tagtgccatt tgttcagtgg ttcgcagggc ttccccccac   120
```

<210> SEQ ID NO 15
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 15

```
tgtttggctt tcagttatat ggatgatgtg gtattggggg ccaagtctgt acaacatctt    60
gaggcccttt atacctctat taccaatttt cttgtgtctt tgggtataca tttgaaccct   120
```

<210> SEQ ID NO 16
<211> LENGTH: 120
<212> TYPE: DNA
<213> ORGANISM: Artificial Sequence

```
<220> FEATURE:
<223> OTHER INFORMATION: Synthetic Polynucleotide

<400> SEQUENCE: 16
aataaaacca aacgttgggg ctactcccctt aacttcatgg gatatgtaat tggaagttgg    60
ggtactttac cacaggaaca tattgtacaa aaaattaagc aatgttttcg gaaactgcct   120

<210> SEQ ID NO 17
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 17
gtcaatagac ctattgattg gaaagtatgt caaagaattg taggtctttt gggatttgct    60 gccccttta cacaatgtgg ctatcctgct ttgatgcctt tatatgcatg tatacaagct   120

<210> SEQ ID NO 18
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 18
aagcaggctt tcactttctc gtcaacttac aaggcctttc tgtgtaaaca atatctgcac    60
ctttaccccg ttgcccggca acggtcaggt ctctgccaag tgtttgctga cgcaaccccc   120

<210> SEQ ID NO 19
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 19
actggatggg gcttggccat aggccatcgg cgcatgcgtg gaacctttgt ggctcctctg    60
ccgatccata ctgcggaact cctagcagct tgttttgctc gcagccggtc tggagcaaac   120

<210> SEQ ID NO 20
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 20
cttatcggga ctgacaactc tgttgtcctc tctcggaaat acacctcctt cccatggctg    60
ctcgggtgtg ctgccaactg gatcctgcgc gggacgtcct ttgtctacgt cccgtcggcg   120

<210> SEQ ID NO 21
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 21
ctgaatcccg cggacgaccc gtctcggggc cgtttgggcc tctaccgtcc ccttcttcat    60
ctgccgttcc ggccgaccac ggggcgcacc tctctttacg cggtctcccc gtctgtgcct   120
```

<210> SEQ ID NO 22
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 22
tctcatctgc cggtccgtgt gcacttcgct tcacctctgc acgtcgcatg gaaaccaccg    60
tgaacgccca tccggtcttg cccaaggtct tatataagag gactcttgga ctctcagcaa   120

<210> SEQ ID NO 23
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 23
tgtcaacgac cgaccttgag gcatacttca aagactgttt gtttaaagac tgggaggagt    60
tgggggagga gaataggtta atgatctttg tactaggagg ctgtaggcat aaattggtct   120

<210> SEQ ID NO 24
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 24
ctcatcggga ctgacaactc ggttgttctc tctcggaaat acacctcatt cccatggctg    60
ctcgggtgtg ctgccaactg gatcctgcgc gggacgtcct ttgtttacgt cccgtcggcg   120

<210> SEQ ID NO 25
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 25
gttcaccagc accatgcaac ttttttcacct ctgcctaatc atctcttgtt catgtcctac    60
tgttcaagcc tccaagctgt gccttgggtg gctttaggac atggacattg acccgtataa   120

<210> SEQ ID NO 26
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 26
agaatttgga gcttctgtgg agttgctctc tttttttgcct tctgacttct ttccttctat    60
tcgagatctc ctcgacaccg cctctgctct ctatcgggag gccttagagt ctccggaaca   120

<210> SEQ ID NO 27
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 27
ttgttcacct caccatacag cactcaggca agctattctg tgttggggtg agttgatgaa      60
cctggccacc tgggtgggaa gtaatttgga agatcctgca tccagggaat tagtagtcag     120

<210> SEQ ID NO 28
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 28
ctatgtcaat gttaatatgg gcctaaaact cagacaaata ttgtggtttc acatttcctg      60
tcttactttt ggaagagaaa ccgttcttga gtatttggtg tcttttggag tgtggattcg     120

<210> SEQ ID NO 29
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 29
cactcctacc gcttacagac caccaaatgc ccctatctta tcaacacttc cggaaactac      60
tgttgttaga cgacgaggca ggacccctag aagaagaact ccctcgcctc gcagacgaag     120

<210> SEQ ID NO 30
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 30
atctcaatcg ccgcgtcgca gaagatctca atctcgggaa tctcaatgtt agtatcccct      60
ggactcacaa ggtgggaaat tttactgggc tttactcgtc tactgtacct atctttaatc     120

<210> SEQ ID NO 31
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 31
ctgattggca aactccctcc tttcctaaca ttcatttaca ggaggacatt attgatagat      60
gtcaacaata tgtaggccct cttacagtta atgaaaaaag gagattaaaa ttaattatgc     120

<210> SEQ ID NO 32
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 32
ctgctaggtt ttatcctaac cttaccaaat atttgcccct ggataaaggc attaaacctt      60
attatcctga acatgcagtt aatcattact tccaaactag gcattattta catactctgt     120

<210> SEQ ID NO 33
<211> LENGTH: 120
<212> TYPE: DNA

<213> ORGANISM: Artificial Sequence
<220> FEATURE:
<223> OTHER INFORMATION: Synthetic Polynucleotide

<400> SEQUENCE: 33

```
ggaaggctgg cattctatat aagagagaaa ctacacgcag cgcttcattt tgtgggtcac      60
catattcttg ggaacaagag ctacagcatg ggaggttggt cttccaaacc tcgacaaggc     120
```

<210> SEQ ID NO 34
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 34

```
atggggacga atctttctgt tcccaatcct ctgggattct ttcccgatca ccagttggac      60
cctgcgttcg gagccaactc aaacaatcca gattgggact caaccccaa caaggatcac     120
```

<210> SEQ ID NO 35
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 35

```
ctgaatcccg cggacgaccc gtctcgcggc cgtttgggcc tctaccgtcc ccttcttcat      60
ctgccgttcc ggccgaccac ggggcgcacc tctctttacg cggtctcccc gtctgtgcct     120
```

<210> SEQ ID NO 36
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 36

```
tggccagagg caaatcaggt cggagtggga gcattcgggc cagggttcac cccaccacac      60
ggcggtcttt tggggtggag ccctcaggct cggggcatag tgacaccagt gccagcagcg     120
```

<210> SEQ ID NO 37
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 37

```
actggggacc ctgcaccgaa catggagaac acaacatcag gattcctagg acccctgctc      60
gtgttacagg cggggttttt cttgttgaca agaatcctca aataccaca gagtctagac     120
```

<210> SEQ ID NO 38
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 38

```
tcgtggtgga cttctctcaa tttcctaggg ggaacaccca cgtgtcctgg ccaaaattcg      60
cagtccccaa cctccaatca ctcaccaacc tcttgtcctc caatttgtcc tggctatcgc     120
```

<210> SEQ ID NO 39
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 39
tggatgtgtc tgcggcgttt tatcatattc ctcttcatcc tgctgctatg cctcatcttc    60
ttgttggttc ttctggacta ccaaggtatg ttgcccgttt gtcctctact tccaggaaca   120

<210> SEQ ID NO 40
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 40
tcaactacca gcacgggacc atgcaagacc tgcacgattc ctgctcaagg cacctctatg    60
tttccctctt gttgctgtac aaaaccttcg gatggaaact gcacttgtat tcccatccca   120

<210> SEQ ID NO 41
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 41
tcatcctggg ttttcgcaag attcctatgg gagtgggcct cagtccgttt ctcctggctc    60
agtttactag tgccatttgt tcagtggttc gtagggcttt cccccactgt ttggctttca   120

<210> SEQ ID NO 42
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 42
gttatatgga tgatatagta ttgggggcca agtctgtaca acatcttgag tcccttata    60 ccgccattac caattttctt ttgtctttgg gtatacattt gaaccctaat aaaaccaaac   120

<210> SEQ ID NO 43
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 43
gttggggcta ctccctgaac ttcatgggat atgtaattgg aagttggggt actttaccgc    60
aagaccatat tgtactaaaa ctcaagcaat gttttcgaaa actgcctgta aatagaccta   120

<210> SEQ ID NO 44
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 44
ttgattggaa agtatgtcag agaattgtgg gtcttttggg ctttgctgcc ccttttacac    60
aatgtggcta tcctgcctta atgcctttat atgcatgtat acaatctaag caggctttca   120

<210> SEQ ID NO 45
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 45
tctcatctgc cggaccgtgt gcacttcgct tcacctctgc acgtcgcatg gagaccaccg    60
tgaacgccca tcaggtcttg cccaaggtct tacataagag gactcttgga ctctcagcaa   120

<210> SEQ ID NO 46
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 46
tggctattgg ccatcagcgc atgcgtggaa cctttgtggc tcctctgccg atccatactg    60
cggaactcct agcagcttgt tttgctcgca gccggtctgg agcgaaactg atcggaacgg   120

<210> SEQ ID NO 47
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 47
acaactctgt tgttctctct cggaaataca cctcctttcc atggctgcta gggtgtgctg    60
ccaactggat cctgcgcggg acgtcctttg tttacgtccc gtcggcgctg aatcccgcgg   120

<210> SEQ ID NO 48
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 48
acgacccatc tcggggccgt ttgggtctct accgtcccct tcttcatctg ccgttccggc    60
cgaccacggg gcgcacctct ctttacgcgg tctccccgtc tgtgccttct catctgccgg   120

<210> SEQ ID NO 49
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 49
accgtgtgca cttcgcttca cctctgcacg tcgcatggag accaccgtga acgcccacca    60
ggtcttgccc aaggtcttat ataagaggac tcttggactc tcagcaatgt caacgaccga   120

<210> SEQ ID NO 50
<211> LENGTH: 120

<212> TYPE: DNA
<213> ORGANISM: Artificial Sequence
<220> FEATURE:
<223> OTHER INFORMATION: Synthetic Polynucleotide

<400> SEQUENCE: 50
ccttgaggca tacttcaaag actgtttgtt taaggactgg gaggagttgg gggaggagtt        60
taggttaatg atctttgtac taggaggctg taggcataaa ttggtctgtt caccagcacc       120

<210> SEQ ID NO 51
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 51
atgcaacttt ttcacctctg cctaatcatc tcatgttcat gtcctactgt tcaagcctcc        60
aagctgtgcc ttgggtggct ttggggcatg acattgacc cgtataaaga atttggagct       120

<210> SEQ ID NO 52
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 52
tctgtggagt tactctcttt tttgccttct gacttctttc cttctattcg agatctcctc        60
gacaccgcct ctgctctgta tcgggaggcc ttagagtctc cggaacattg ttcacctcac       120

<210> SEQ ID NO 53
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 53
catacagcaa tcaggcaagc tattctgtgt tggggtgagt tgatgaatct ggccacctgg        60
gtgggaagta atttggaaga cccagcatcc agggaattag tagtcagcta tgtcaatgtt       120

<210> SEQ ID NO 54
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 54
aatatgggcc taaaaatcag acaactactg tggtttcaca tttcctgtct tactttggga        60
agagaaactg ttcttgagta tttggtgtct tttggagtgt ggattcgcac tcctcccgct       120

<210> SEQ ID NO 55
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 55
tgtcaacgtc cgaccttgag gcatacttca aagactgttt gtttaaggac tgggaggagt        60
tgggggagga gattaggtta aaggtctgga ggctgtaggc ataaattggt ctgttcacca    120

<210> SEQ ID NO 56
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 56
tacagaccac caaatgcccc tatcttatca acacttccgg aaactactgt tgttagacga    60
cgaggcaggt ccctagaag aagaactccc tcgcctcgca gacgaaggtc tcaatcgccg    120

<210> SEQ ID NO 57
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 57
cgtcgcagaa gatctcaatc tcgggaatct caatgttagt atcccttgga ctcataaggt    60
gggaaacttt actgggcttt attcttctac tgtacctgtc tttaatcctg agtggcaaac    120

<210> SEQ ID NO 58
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 58
tccctccttt cctcacattc atttgcagga ggacattatt aatagatgtc aacaatatgt    60
gggccctctt acagttaatg aaaaaaggag attaaaatta attatgcctg ctaggttcta    120

<210> SEQ ID NO 59
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 59
tcctaacctt accaaatatt tgcccttgga caaaggcatt aaaccatatt atcctgaaca    60
tgcagttcat cattacttca aaactaggca ttatttacat actctgtgga aggctggcat    120

<210> SEQ ID NO 60
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 60
tctatataag agagaaacta cacgcagcgc ctcattttgt gggtcaccat attcttggga    60
acaagagcta cagcaaacct cgacaaggca tggggacaaa tctttctgtt cccaatcctc    120

<210> SEQ ID NO 61
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 61
tgggattctt tcccgatcac cagttggacc ctgcgttcgg agccaactca acaatccag    60 attgggactt caaccccaac aaggatcact ggccagaggc aaatcaggta ggagcgggag    120

<210> SEQ ID NO 62
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 62
ctccaccaca ttccaccaag ctctgctaca ccccagagta aggggcctat actttcctgc    60
tggtggctcc agttccggaa cagtaaaccc tgttccgact actgcctctc ccatatcgtc    120

<210> SEQ ID NO 63
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 63
aatcttctcg aggactgggg accctgcacc gaacatggag aacacaacat caggattcct    60
aggacccctg ctcgtgttac aggcggggtt tttcttgttg acaagaatcc tcacaatacc    120

<210> SEQ ID NO 64
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 64
acagagtcta gactcgtggt ggacttctct caattttcta gggggagcac ccacgtgtcc    60
tggccaaaat tcgcagtccc caacctccaa tcactcacca acctcttgtc ctccaatttg    120

<210> SEQ ID NO 65
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 65
tcctggctat cgctggatgt gtctgcggcg ttttatcata ttcctcttca tcctgctgct    60
atgcctcatc ttcttgttgg ttcttctgga ctaccaaggt atgttgcccg tttgtcctct    120

<210> SEQ ID NO 66
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 66
gcaccatgca acttttcac ctctgcctaa tcatctcatg ttcatgtcct actgttcaag    60
cctccaagct gtgccttggg tggctttggg gcatggacat tgacccgtat aaagaatttg    120

<210> SEQ ID NO 67

<210> SEQ ID NO 67
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 67
acttccagga acatcaacta ccagcacggg accatgcaag acctgcacga ttcctgctca    60
aggcacctct atgtttccct cttgttgctg tacaaaacct tcggacggaa actgcacttg   120

<210> SEQ ID NO 68
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 68
tattcccatc ccatcatcct gggctttcgc aagattccta tgggagtggg cctcagtccg    60
tttctcctgg ctcagtttac tagtgccatt tgttcagtgg ttcgtagggc tttcccccac   120

<210> SEQ ID NO 69
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 69
tgtttggctt tcagttatat ggatgatgtg gtattggggg ccaagtctgt acaacatctt    60
gagtcccttt ttaccgctgt taccaatttt cttttgtctt tgggtataca tttgaaccct   120

<210> SEQ ID NO 70
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 70
aataaaacca aacgttgggg ttactcccctt aacttcatgg gatatgtaat tggaagttgg    60
ggtactttac cgcaagacca tattgtacta aaaatcaagc aatgttttcg aaaactgcct   120

<210> SEQ ID NO 71
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 71
gtaaatagac ctattgattg gaaagtatgt cagagaattg tgggtctttt gggctttgct    60 gccccttta cacaatgtgg ctatcctgcc ttaatgcctt tatatgcatg tatacaatct   120

<210> SEQ ID NO 72
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 72
aagcaggctt tcactttctc gccaacttac aaggcctttc tgtgtaaaca atatctgaac    60 ctttacccccg ttgcccggca acggtcaggt ctctgccaag tgtttgctga cgcaacccccc    120

<210> SEQ ID NO 73
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 73
actggatggg gcttggctat tggccatcgc cgcatgcgtg gaacctttgt ggctcctctg    60
ccgatccata ctgcggaact cctagcagct tgttttgctc gcagccggtc tggagcgaaa    120

<210> SEQ ID NO 74
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 74
ctgatcggaa cggacaactc tgttgttctc tctcggaaat acacctcctt tccatggctg    60
ctagggtgtg ctgccaactg gatcctgcgc gggacgtcct ttgtttacgt cccgtcggcg    120

<210> SEQ ID NO 75
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 75
ctgaatcccg cggacgaccc atctcggggc cgtttgggtc tctaccgtcc ccttcttcat    60
ctgccgttcc ggccgaccac ggggcgcacc tctctttacg cggtctcccc gtctgtgcct    120

<210> SEQ ID NO 76
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 76
tctcatctgc cggaccgtgt gcacttcgct tcacctctgc acgtcgcatg gagaccaccg    60
tgaacgccca ccaggtcttg cccaaggtct tatataagag gactcttgga ctctcagcaa    120

<210> SEQ ID NO 77
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 77
gagcttctgt ggagttactc tcttttttgc cttctgactt ctttccttcc attcgagatc    60
tcctcgacac cgcctctgct ctgtatcggg aggccttaga gtctccggaa cattgttcac    120

<210> SEQ ID NO 78
<211> LENGTH: 120
<212> TYPE: DNA
<213> ORGANISM: Artificial Sequence
<220> FEATURE:

<223> OTHER INFORMATION: Synthetic Polynucleotide

<400> SEQUENCE: 78
tgtcaacgac cgaccttgag gcatacttca aagactgttt gtttaaggac tgggaggagt    60
tgggggagga gattaggtta atgatctttg tactaggagg ctgtaggcat aaattggtct    120

<210> SEQ ID NO 79
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 79
gttcaccagc accatgcaac tttttcacct ctgcctaatc atctcatgtt catgtcctac    60
tgttcaagcc tccaagctgt gccttgggtg gctttaggac atggacattg acccatataa    120

<210> SEQ ID NO 80
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 80
agaatttgga gcttctgtgg agttactctc ttttttgcct tctgactttt ttccttctat    60
tcgagatctc ctcgacaccg cctctgctct gtatcgggag gccttagagt ctccggaaca    120

<210> SEQ ID NO 81
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 81
ttgttcacct caccatacag cactcagaca agccattctg tgttggggtg agttgatgaa    60
tctggccacc tgggtgggaa gtaatttgga agacccagca tccagggaat tagtagtcag    120

<210> SEQ ID NO 82
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 82
ctatgtcaat gttaatatgg gcctaaaaat cagacaacta ctgtggtttc acatttcctg    60
tcttactttt ggaagagaaa ctgttcttga gtatttggtg tcttttggag tgtggattcg    120

<210> SEQ ID NO 83
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 83
cactcctcct gcttacagac catcaaatgc ccctatctta tcaacacttc cggaaactac    60
tgttgttaga cgacgaggca ggtcccctag aagaagaact ccctcgcctc gcagacgaag    120

<210> SEQ ID NO 84
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 84
gtctcaatcg ccgcgtcgca gaagatctca atctcgggaa cctcaatgtt agtatccctt      60
ggactcataa ggtgggaaac tttactgggc tttattcttc tactgtacct gtctttaatc     120

<210> SEQ ID NO 85
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 85
ctgagtggca aactccctct tttcctcata ttcatttgca ggaggacatt attaatagat      60
gtcaacaata tgtgggccct cttacagtta atgaaaaaag gagattaaaa ttaattatgc     120

<210> SEQ ID NO 86
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 86
ctgctaggtt ctatcctaac cttaccaaat atttgcccctt ggacaaaggc attaaaccat     60
attatccgga acatgcagtt aatcattact tcaaaactag gcattattta catactctgt     120

<210> SEQ ID NO 87
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 87
ctcaccatac agcactcagg caagctattc tctgttgggg tgagttgatg aatctggcca     60
cctgggtggg aagtaatttg gaagacccag catccaggga tttagtagtc agctatgtca    120

<210> SEQ ID NO 88
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 88
atggggacaa atctttctgt tcccaatcct ctgggattct ttcccgatca ccagttggac     60
cctgcgttcg gagccaactc aaacaatcca gattgggact tcaaccccaa caaggatcac    120

<210> SEQ ID NO 89
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 89
tggccagagg caaatcaggt aggagcggga gcattcgggc cagggttcac cccaccacac    60
ggcggtcttt tggggtggag ccctcaggct cagggcacat tgacaacagt gccagtagca    120

<210> SEQ ID NO 90
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 90
ctccacaaca ttccaccaag ctctgctaga tcccagagtg aggggcctat attttcctgc    60
tggtggctcc agttccggaa cagtaaaccc tgttccgact actgcctcac ccatatcgtc    120

<210> SEQ ID NO 91
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 91
aatcttctcg aggactgggg accctgcacc gaacatggag agcacaacat caggattcct    60
aggacccctg ctcgtgttac aggcggggtt tttcttgttg acaagaatcc tcacaatacc    120

<210> SEQ ID NO 92
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 92
acagagtcta gactcgtggt ggacttctct caattttcta ggggagcac ccacgtgtcc    60 tggccaaaat tcgcagtccc caacctccaa tcactcacca acctcttgtc ctccaatttg    120

<210> SEQ ID NO 93
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 93
tcctggctat cgctggatgt gtctgcggcg ttttatcata ttcctcttca tcctgctgct    60
atgcctcatc ttcttgttgg ttcttctgga ctaccaaggt atgttgcccg tttgtcctct    120

<210> SEQ ID NO 94
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 94
acttccagga acatcaacta ccagcacggg accatgcaag acctgcacga ttcctgctca    60
aggaacctct atgtttccct cttgttgctg tacaaaacct tcggacggaa actgcacttg    120

<210> SEQ ID NO 95
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 95
tattcccatc ccatcatcct gggctttcgt aaaattccta tgggagtggg cctcagtccg    60
tttctcctgg ctcagtttac tagtgccatt tgttcagtgg ttcgcagggc tttcccccac   120

<210> SEQ ID NO 96
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 96
tgtttggctt tcagttatat ggatgatgtg gtattgggggg ccaagtctgt gcaacatctt    60
gagtcccttt ttacctctat taccaatttt cttttgtctt tgggtataca tttgaaccct   120

<210> SEQ ID NO 97
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 97
aataaaacca aacgttgggg ctactccctt aacttcatgg gatatgtaat tggaagttgg    60
ggtactttac cacaggaaca tattgtatta aaactcaagc aatgttttcg gaaattgcct   120

<210> SEQ ID NO 98
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 98
atgttaatat gggcctaaaa atcagacaac tattgtggtt tcacatttcc tgtcttactt    60
ttggaagaga aactgttctt gagtatttgg tgtcttttgg agtgtggatt cgcactcctc   120

<210> SEQ ID NO 99
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 99
gtaaatagac ctattgattg gaaagtatgt caaagaattg tgggtctttt ggactttgct    60
gcccctttta cacaatgtgg ctatcctgca ttgatgcctt tatatgcatg tatacaagct   120

<210> SEQ ID NO 100
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 100
aagcaggctt tcactttctc gccaacttac aaggcctttc tgtgtcaaca atacctgcac    60 ctttacccccg ttgcccggca acggtcaggt ctctgccaag tgtttgctga cgcaaccccc   120

<210> SEQ ID NO 101
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 101
actggatggg gcttggccat aggccatcgg cgcatgcgtg gaacctttgt ggctcctctg    60
ccgatccata ctgcggaact cctagcggct tgttttgctc gcagccggtc tggagcaaaa   120

<210> SEQ ID NO 102
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 102
cttatcggga ccgacaactc tgttgtcctc tctcggaaat acacctcctt cccatggctg    60
ctcgggtgtg ctgccaactg gatcctgcgc gggacgtcct ttgtctacgt cccgtcggcg   120

<210> SEQ ID NO 103
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 103
ctgaatcccg cggacgaccc gtctcgggc cgtttgggcc tctatcgtcc ccttcttcat    60
ctgccgttcc agccgaccac ggggcgcacc tctctttacg cggtctcccc gtctgtgcct   120

<210> SEQ ID NO 104
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 104
tctcatctgc cggaccgtgt gcacttcgct tcacctctgc acgtcgcatg gaaaccaccg    60
tgaacgccca tcaggtcttg cccaagctct tacataagag gactcttgga ctctcagcaa   120

<210> SEQ ID NO 105
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 105
tgtcaacgac cgaccttgag gcttacttca aagactgttt gtttaaagac tgggaggagt    60
tgggggagga gactaggtta aaggtctttg tactaggagg ctgtaggcat aaattggtct   120

<210> SEQ ID NO 106
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 106

```
gttcaccagc accatgcaac tttttcacct ctgcctaatc atctcatgtt catgtcctac    60
tgttcaagcc tccaagctgt gccttgggtg gctttggggc atggacattg acccgtataa   120
```

<210> SEQ ID NO 107
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 107

```
agaatttgga gcttctgcgg agttactctc tttttttgcct tctgacttct ttccttctat    60
tcgagatctc ctcgacaccg cctctgctct atatcgggag gccttagagt ctccggaaca   120
```

<210> SEQ ID NO 108
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 108

```
ttgttcacct caccatacag cactcaggca agctattctg tgttggggtg agttgatgaa    60
tctggccacc tgggtgggaa gtaatttgga agacccagca tccagggaat tagtagtcag   120
```

<210> SEQ ID NO 109
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 109

```
aatcttctcg aggactgggg accctgcacc gaacatggag agcacaacat caggattcct    60
aggacccctg ctcgtgttac aggcggggtt tttcttgttg acaagaatcc tcacaatacc   120
```

<210> SEQ ID NO 110
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 110

```
ccgcttacag accaccaaat gcccctatct tatcaacact tccggaaact actgttgtta    60
gacgacgagg caggtcccct agaagaagaa ctccctcgcc tcgcagacga aggtctcaat   120
```

<210> SEQ ID NO 111
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 111

```
ctatgtcaat gttaatatgg gcctaaaaat cagacaacta ttgtggtttc acatttcctg    60
tcttactttt ggaagagaaa ctgttcttga gtatttggtg tcttttggag tgtggattcg   120
```

<210> SEQ ID NO 112
<211> LENGTH: 120
<212> TYPE: DNA

<213> ORGANISM: Artificial Sequence
<220> FEATURE:
<223> OTHER INFORMATION: Synthetic Polynucleotide

<400> SEQUENCE: 112
cactcctccc gcttacagac caccaaatgc ccctatctta tcaacacttc cggaaactac    60
tgttgttaga cgacgaggca ggtcccctag aagaagaact ccctcgcctc gcagacgaag   120

<210> SEQ ID NO 113
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 113
gtctcaatcg ccgcgtcgca gaagatctca atctcgggaa tctcaatgtt agtatcccctt   60
ggactcataa ggtgggaaac tttactgggc tttattcttc tactgtacct gtctctaatc   120

<210> SEQ ID NO 114
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 114
ctgagtggca aactccctcc tttcctaaca ttcatttaca ggaggacgtt attaatagat    60
gtcaacaata tgtgggccct cttacagtta atgaaaaaag gagattaaaa ttaattatgc   120

<210> SEQ ID NO 115
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 115
ctgctaggtt ctatcctaac cttaccaaat atttgccctt ggataaaggc attaaacctt    60
attatcctga acatgcagtt aatcattact tcaaaactag gcattattta catactctgt   120

<210> SEQ ID NO 116
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 116
ggaaggctgg cattctatat aaaagagaaa ctacacgcag cgcttcattt tgtgggtcac    60
catattcttg ggaacaagag ctacagcatg ggaggttggt cttccaaacc tcgacaaggc   120

<210> SEQ ID NO 117
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 117
atggggacga atctttctgt tcccaatcct ctgggattct ttcccgatca ccagttggac    60
cctgcgttca gagccaactc aaacaatcca gattgggact tcaaccccaa caaggatcac   120

<210> SEQ ID NO 118
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 118
tggccagagg caaatcaggt aggagcggga gcattcgggc cagggttcac cccaccacac    60
ggcggtcttt tggggtggag ccctcaggct cagggcatat tgacaactgt gccagcagcg   120

<210> SEQ ID NO 119
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 119
catattgaca acagtgccag cagcgcctcc tcctgcctcc accaatcggc agtcaggaag    60
acagcctact cccatctctc cacctctaag agacagtcat cctcaggcca tgcagtggaa   120

<210> SEQ ID NO 120
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 120
catattgaca acagtgcccg cagcgcctcc tcctgcctcc accaatcggc agttaggaag    60
acagcctact cccatctctc cacctctaag agacagtcat cctcaggcca tgcagtggaa   120

<210> SEQ ID NO 121
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 121
cgccgcgtcg cagaagatct caatctcggg aatctcaatg ttagtatccc ttggactcat    60
aaggtgggaa actttactgg gctttattct tctactgtac ctgtctttaa tcctgagtgg   120

<210> SEQ ID NO 122
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 122
catattgaca acagtgccag cagcgcctcc tcctgcctcc accaatcggc agtcaggaag    60
acagcctact cccatctctc cacctctaag agacagtcat cctcaggcca tgcagtggaa   120

<210> SEQ ID NO 123
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 123
catattgaca accgtgccag tagcacctcc tcctgcctcc accaatcggc agtcaggaag    60
acagcctact cccatctctc cacctctaag agacagtcat cctcaggcca tgcagtggaa   120

<210> SEQ ID NO 124
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 124
catagtgaca ccagtgccag cagcgcctcc tcctgcctcc accaatcggc agtcaggaag    60
acagcctact cccatctctc cacctctaag agacagtcat cctcaggcca tgcagtggaa   120

<210> SEQ ID NO 125
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 125
gcattcgggc cagggttcac cccaccacac ggcggtcttt tggggtggag ccctcaggct    60
cagggtgcat tgacaacagt gccagtagca cctcctcctg cctccaccaa tcggcagcct   120

<210> SEQ ID NO 126
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 126
cacattgaca acagtgccag tagcacctcc tcctgcctcc accaatcggc agtcaggaag    60
acagcctact cccatctctc cacctctaag agacagtcat cctcaggcca tgcagtggaa   120

<210> SEQ ID NO 127
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 127
catattgaca actgtgccag cagcgcctcc tcctgcctcc accaatcggc agtcagaaag    60
acagcctact cccatctctc cacctctaag agacagtcat cctcaggcca tgcagtggaa   120

<210> SEQ ID NO 128
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 128
caaactccct cctttcctaa cattcattta caggaagaca ttattaatag atgtcaacaa    60
tatgtgggcc ctcttacagt taatgaaaaa aggagattaa aattaattat gcctgctagg   120

<210> SEQ ID NO 129
<211> LENGTH: 120

```
<212> TYPE: DNA
<213> ORGANISM: Artificial Sequence
<220> FEATURE:
<223> OTHER INFORMATION: Synthetic Polynucleotide

<400> SEQUENCE: 129
ttctatccta accttaccaa atatttgccc ttggataaag gcattaaacc ttattatcct      60
gaacatgcag ttaatcatta cttcaaaact aggcattatt tacatactct gtggaaggct     120

<210> SEQ ID NO 130
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 130
ggcattctat ataaaagaga aactacacgc agcgcttcat tttgtgggtc accatattct     60
tgggaacaag agctacagca tgggaggttg gtcttccaaa cctcgacaag gcatgggac     120

<210> SEQ ID NO 131
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 131
gaatctttct gttcccaatc ctctgggatt ctttcccgat caccagttgg accctgcgtt     60
cggagccaac tcaaacaatc cagattggga cttcaacccc aacaaggatc actggccaga    120

<210> SEQ ID NO 132
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 132
ggcaaatcag gtaggagcgg gagcattcgg gccagggttc accccaccac acggcggtct     60
tttggggtgg agccctcagg ctcagggcat attgacaaca gtgccagcag cgcctcctcc    120

<210> SEQ ID NO 133
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 133
ctccacaaca ttccaccaag ctctgctaga tcccagagtg aggggcctat attttcctgc     60
tggtggctcc agttccggaa cagtaaaccc tgttccgact actgcctcac ccatatcgtc    120

<210> SEQ ID NO 134
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 134
aatcttctcg aggactgggg accctgcacc gaacatggag aacacaacat caggattcct     60
```
aggacccctg ctcgtgttac aggcggggtt tttcttgttg acaagaatcc tcacaatacc    120

<210> SEQ ID NO 135
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 135
acagagtcta gactcgtggt ggacttctct caattttcta ggggaagcac ccacgtgtcc    60
tggccaaaat tcgcagtccc caacctccaa tcactcacca acctcttgtc ctccaatttg   120

<210> SEQ ID NO 136
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 136
acagagtcta gactcgtggt ggacttctct caattttcta gggggagcac ccacgtgtcc    60
tggccaaaat tcgcagtccc caacctccaa tcactcacca acctcttgtc ctccaatttg   120

<210> SEQ ID NO 137
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 137
tcctggctat cgctggatgt gtctgcggcg ttttatcata ttcctcttca tcctgctgct    60
atgcctcatc ttcttgttgg ttcttctgga ctaccaaggt atgttgcccg tttgtcctct   120

<210> SEQ ID NO 138
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 138
acttccagga acatcaacta ccagcacggg accatgcaag acctgcacga ttcctgctca    60
aggaacctct atgtttccct cttgttgctg tacaaaacct tcggacggaa actgcacttg   120

<210> SEQ ID NO 139
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 139
tattcccatc ccatcatcct gggctttcgc aaaattccta tgggagtggg cctcagtccg    60
tttctcctgg ctcagtttac tagtgccatt tgttcagtgg ttcgcagggc tttcccccac   120

<210> SEQ ID NO 140
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 140
tgtttggctt tcagttatat ggatgatgtg gtattggggg ccaagtctgt acaacatctt    60
gagtcccttt ttacctctat taccaatttt cttttgtctt tgggtataca tttgaaccct   120

<210> SEQ ID NO 141
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 141
aataaaacca aacgttgggg ctactccctt aacttcatgg gatatgtaat tggaagttgg    60
ggtactttac cacaggaaca tattgtacta aaaatcaagc aatgttttcg gaaactgcct   120

<210> SEQ ID NO 142
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 142
gtaaatagac ctattgattg gaaagtatgt caaagaattg tgggtctttt gggctttgct    60 gccccttta cacaatgtgg ctatcctgcc ttgatgcctt tatatgcatg tatacaatct   120

<210> SEQ ID NO 143
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 143
aagcaggctt tcactttctc gccaacttac aaggcctttc tgtgtaaaca atatctgcac    60
ctttaccccg ttgcccggca acggtcaggt ctctgccaag tgtttgctga cgcaaccccc   120

<210> SEQ ID NO 144
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 144
cttatcggga ctgacaactc tgttgtcctc tctcagaaat acacctcctt cccatggctg    60
ctcgggtgtg ctgccaactg gatcctgcgc gggacgtcct ttgtctacgt cccgtcggcg   120

<210> SEQ ID NO 145
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 145
tcctggctat cgctggatgt gtctgcggcg ttttatcata ttcctcttca tcctgctgct    60
atgcctcatc ttcttgttgg ttcttctgga ctaccaaggt atgttgcccg tttgtcctct   120

<210> SEQ ID NO 146

```
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 146
tctcatctgc cggtccgtgt gcacttcgct tcacctctgc acgtcgcatg gagaccaccg      60
tgaacgccca ccaggtcttg cccaaggtct tacataagag gactcttgga ctctcagcaa     120

<210> SEQ ID NO 147
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 147
tgtcaacaac cgaccttgag gcatacttca aagactgttt gtttaaagac tgggaggagt      60
tgggggagga gattaggtta aaggtctttg tactaggagg ctgtaggcat aaattggtct     120

<210> SEQ ID NO 148
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 148
gttcaccagc accatgcaac tttttcacct ctgcctaatc atctcatgtt catgtcctac      60
tgttcaagcc tccaagctgt gccttgggtg gctttgggc atggacattg acccgtataa     120

<210> SEQ ID NO 149
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 149
agaatttgga gcttctgtgg agttactctc ttttttgcct tctgacttct ttccttctat      60
tcgagatctc ctcgacaccg cctctgctct gtatcgggag gccttagagt ctccggaaca     120

<210> SEQ ID NO 150
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 150
ttgttcacct caccatacag cactcaggca agctattctg tgttggggtg agttattgaa      60
tctggccacc tgggtgggaa gtaatttgga agacccagca tccagggaat tagtagtcag     120

<210> SEQ ID NO 151
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 151
ctatgtcaat gttaatatgg gcctaaaaat cagacaacta ttgtggtttc acatttcctg      60
```

```
tcttactttt ggaagagaaa ctgttcttga gtatttggtg tcttttggag tgtggattcg    120
```

<210> SEQ ID NO 152
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 152

```
gtctcaatcg ccgcgtcgcc gaagatctca atctcgggaa tctcaatgtt agtatccctt    60
ggactcataa ggtgggaaac tttactgggc tttattcttc tactgtacct gtctttaatc   120
```

<210> SEQ ID NO 153
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 153

```
ctgagtggca aactccctcc tttcctaaca ttcatttaca ggaggacatt attaatagat    60
gtcaacaata tgtgggccct ctcacagtta atgaaaaaag gagattaaaa ttaattatgc   120
```

<210> SEQ ID NO 154
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 154

```
acttccagga acatcaacta ccagcacggg accatgcaag acctgcacga ttcctgctca    60
aggaacctct atgtttccct cttgttgctg tacaaaacct tcggacggaa actgcacttg   120
```

<210> SEQ ID NO 155
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 155

```
atggggacga atctttctgt tcccaatcct ctgggattct ttcccgatca ccagttggac    60
cctgcgttcg gagccaactc aaacaatcca gattgggact tcaaccccaa caaggatcac   120
```

<210> SEQ ID NO 156
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 156

```
tggccagagg caaatcaggt aggagcggga gcattcgggc cagggttcac cccaccacac    60
ggcggtcttt tggggtggag ccctcaggct caggcatat tgacaacagt gcccgcagcg    120
```

<210> SEQ ID NO 157
<211> LENGTH: 120
<212> TYPE: DNA
<213> ORGANISM: Artificial Sequence
<220> FEATURE:

<223> OTHER INFORMATION: Synthetic Polynucleotide

<400> SEQUENCE: 157

```
ctccacaaca ttccaccaag ctctgctaga tcccagagtg aggggcctat attttcctgc      60
tggtggctcc agttccggaa cagtaaaccc tgttccgact actgcctcac ccatatcgtc     120
```

<210> SEQ ID NO 158
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 158

```
aatcttctcg aggactgggg accctgcacc gaacatggag agcacaacat caggattcct      60
aggacccctg ctcgtgttac aggcggggtt tttcttgttg acaagaatcc tcacatacc      120
```

<210> SEQ ID NO 159
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 159

```
acagagtcta gactcgtggt ggacttctct caattttcta gggggagcac ccacgtgtcc      60
tggccaaaat tcgcagtccc caacctccaa tcactcacca acctcttgtc ctccaatttg     120
```

<210> SEQ ID NO 160
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 160

```
tcctggctat cgctggatgt gtctgcggcg ttttatcata ttcctcttca tcctgctgct      60
atgcctcacc ttcttgttgg tccttctgga ctaccaaggt atgttgcccg tttgtcctct     120
```

<210> SEQ ID NO 161
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 161

```
acttccagga acatcaacta ccagcacggg accatgcaag acctgcacga ctcctgctca      60
aggaacctct atgtttccct cttgttgctg tacaaaacct tcggacggaa actgcacttg     120
```

<210> SEQ ID NO 162
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 162

```
tattcccatc ccatcatcct gggctttcgc aagattccta tgggagtggg cctcagtccg      60
tttctcctgg ctcagtttac tagtgccatt tgttcagtgg ttcgcagggc tttcccccac     120
```

<210> SEQ ID NO 163
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 163
tgtttggctt tcagttatat ggatgatggg gtattgggggg ccaagtctgt acaacatctt    60
gagtcccttt ttacctctat taccaatttt cttttgtctt tgggtataca tttgaaccct   120

<210> SEQ ID NO 164
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 164
tattcccatc ccatcatcct gggctttcgc aagattccta tgggagtggg cctcagtccg    60
tttctcctgg ctcagtttac tagtgccatt tgttcagtgg ttcgtagggc tttcccccac   120

<210> SEQ ID NO 165
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 165
aataaaacca aacgttgggg ctactccctt aacttcatgg gatatgtaat tggaagttgg    60
ggtactttac cacaggaaca tattgtatta aaaatcaaga aatgttttcg gaaactgcct   120

<210> SEQ ID NO 166
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 166
gtaaatagac ctattgattg gaaagtatgt caaagaattg tgggtctttt gggctttgct    60
gcccctttta cacaatgtgg ctatcctgcc ttaatgcctt tatatgcatg tatacaatct   120

<210> SEQ ID NO 167
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 167
aagcaggctt tcactttctc gcccacttac aaggcctttc tgtgtcaaca atacctgcac    60
ctttaccccg ttgcccggca acggtcaggt ctctgccaag tgtttgctga cgcaaccccc   120

<210> SEQ ID NO 168
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 168

```
actggatggg gcttggccat aggccatcgg cgcatgcgtg gaacctttgt ggctcctctg    60
ccgatccata ctgcggaact cctagcagct tgttttgctc gcagccggtc tggagcaaaa   120
```

<210> SEQ ID NO 169
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 169

```
cttatcggga ctgacaactc tgttgtcctc tctcggaaat acacctcctt cccatggctg    60
ctcggatgtg ctgccaactg gatcctgcgc gggacgtcct ttgtctacgt cccgtcggcg   120
```

<210> SEQ ID NO 170
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 170

```
ctgaatcccg cggacgaccc gtctcggggc cgtttgggcc tctaccgtcc ccttcttcat    60
ctgccgttcc agccgaccac ggggcgcacc tctctttacg cggtctcccc gtctgtgcct   120
```

<210> SEQ ID NO 171
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 171

```
tctcatctgc cggtccgtgt gcacttcgct tcacctctgc acgtcgcatg gaaaccaccg    60
tgaacgccca ccaggtcttg cccaaggtct tatataagag gactcttgga ctctcagcaa   120
```

<210> SEQ ID NO 172
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 172

```
tgtcaacgac cgaccttgag gcatacttca aagactgttt gtttaaagac tgggaggagt    60
tgggggagga gattaggtta atgatctttg tactaggagg ctgtaggcat aaattggtct   120
```

<210> SEQ ID NO 173
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 173

```
gttcaccagc accatgcaac ttttcacct ctgcctaatc atctcatgtt catgtcctac    60
tgttcaagcc tccaagctgt gccttgggtg gctttgggc atggacattg accgtataa   120
```

<210> SEQ ID NO 174
<211> LENGTH: 120
<212> TYPE: DNA
<213> ORGANISM: Artificial Sequence

```
<220> FEATURE:
<223> OTHER INFORMATION: Synthetic Polynucleotide

<400> SEQUENCE: 174
agaatttgga gcttctgcgg agttactctc ttttttgcct tctgacttct ttccgtctat    60
tcgagatctc ctcgacaccg cctctgctct gtatagggag gccttagagt ctccggaaca   120

<210> SEQ ID NO 175
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 175
tgtttggctt tcagttatat ggatgatgtg gtattggggg ccaagtctgt acaacatctt    60
gagtcccttt ttacctctat taccaatttt cttgtgtctt tgggtataca tttgaaccct   120

<210> SEQ ID NO 176
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 176
ttgttcacct caccatacag cactcaggca agctattctg tgttggggtg agttgatgaa    60
tctggccacc tgggtgggaa gtaatttgga agacccagca tccagggaat tagtagtcgg   120

<210> SEQ ID NO 177
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 177
ctatgtcaat gttaatatgg gcctaaaact cagacaacta ttgtggtttc acatttcctg    60
tcttactttt ggaagagaaa ctgttcttga gtatttggtg tcttttggag tgtggattcg   120

<210> SEQ ID NO 178
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 178
cactcctacc gcttacagac caccaaatgc ccctatctta tcaacacttc cggaaactac    60
tgttgttaga cgacgaggca ggtcccctag aagaagaact ccctcgcctc gcagacgaag   120

<210> SEQ ID NO 179
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 179
gtctcaatcg ccgcgtcgca gaagatctca atctcgggaa tctcaatgtt agtatccctt    60
ggactcataa ggtgggaaac tttactgggc tttattcttc tactgtacct gtctttaatc   120
```

<210> SEQ ID NO 180
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 180
ctgagtggca aactccctcc tttcctaaca ttcatttaca ggaggacatt attaatagat    60
gtcaacaata tgtgggccct cttacagtta atgaaaaag gagattaaaa ttaattatgc   120

<210> SEQ ID NO 181
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 181
ctgctaggtt ctatcctaac cttaccaaat atttgccctt ggataagggc attaaacctt    60
attatcctga acatgcagtt aatcattact tcaaaactag gcattattta catactctgt   120

<210> SEQ ID NO 182
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 182
ggaaggctgg cattctatat aaagagaaa ctacacgcag cgcttcattt tgtgggtcac    60
catattcttg ggaacaagag ctacagcatg ggaggttggt cttccaaacc tcgaaaaggc   120

<210> SEQ ID NO 183
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 183
atggggacga atctttctgt tcccaatcct ctgggattct ttcccgatca ccagttggac    60
cctgcattcg gagccaactc aaacaatcca gattgggact tcaaccccaa caaggatcac   120

<210> SEQ ID NO 184
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 184
tggccagagg caactcaggt aggagcggga gcattcgggc cagggttcac cccaccacac    60
ggcggtcttt tggggtggag ccctcaggct cagggcatat tgacaacagt gccagcagcg   120

<210> SEQ ID NO 185
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 185

```
ctccacaaca ttccaccaag ctctgctaga ccccagagtg aggggcctat actttcctgc      60
tggtggctcc agttccggaa cagtaaaccc tgttccgact actgcctcac ccatatcgtc     120

<210> SEQ ID NO 186
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 186
aataaaacca aacgttgggg ctactccctt aacttcatgg gatatgtaat tggaagttgg      60
ggtactttac cacaggaaca tattgtacaa aaactcaagc aatgttttcg gaaactgcct     120

<210> SEQ ID NO 187
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 187
aatcttctcg aggactgggg accctgcacc gaacatggag aacacaacat caggattcct      60
aggacccctg ctcgtgttac aggcggggtt tttcttgttg acaagaatcc tcacaatacc     120

<210> SEQ ID NO 188
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 188
acagagtcta gactcgtggt ggacttctct caattttcta gggggagcac ccacgtgtcc      60
tggccaaaat tcgcagtccc caacctccaa tcactcacca acctcttgtc ctccaatttg     120

<210> SEQ ID NO 189
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 189
acctggctat cgctggatgt gtctgcggcg ttttatcata ttcctcttca tcctgctgct      60
atgcctcatc ttcttgttgg ttcttctgga ctaccaaggt atgttgcccg tttgtcctct     120

<210> SEQ ID NO 190
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 190
acttccagga acatcaacta ccagcacagg accatgcaag acctgcacga ttcctgctca      60
aggaacctct atgtttccct cttgttgctg tacaaaacct tcggacggaa actgcacttg     120

<210> SEQ ID NO 191
<211> LENGTH: 120
<212> TYPE: DNA
```

<213> ORGANISM: Artificial Sequence
<220> FEATURE:
<223> OTHER INFORMATION: Synthetic Polynucleotide

<400> SEQUENCE: 191
tattcccatc ccatcatcct gggctttcgc aagattccta tgggagtggg cctcagtccg    60
tttctcctgg ctcagtttac tagtgccatt tgttcagtgg ttcgtagggc ttccccccac   120

<210> SEQ ID NO 192
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 192
tgtttggctt tcagttatat ggatgatgtg gtattggggg ccaagtctgt acaacatctt    60
gagtcccttt ttacctctat tacccatttt cttttatctt tgggtataca tttgaacccc   120

<210> SEQ ID NO 193
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 193
aataaaacca aacgttgggg ctactcccctt aacttcatgg gatatgtaat tggatgttgg   60
ggtactttac cgcaagaaca tattgtacta aaaatcaagc aatgttttcg aaaactgcct  120

<210> SEQ ID NO 194
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 194
gtaaatagac ctattgattg gaaagtatgt cagagaattg tgggtctttt gggctttgct    60 gccccttta cacaatgtgg ctatcctgcc ttaaagcctt tatatgcatg tatacaagct   120

<210> SEQ ID NO 195
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 195
aagcaggctt tcactttctc gccgacttac aaggcctttc tgtgtaaaca atatctgaac    60
ctttaccccg ttgcccggca acggtcaggt ctctgccaag tgtttgctga cgcaaccccc   120

<210> SEQ ID NO 196
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 196
actggctggg gcttggctat cggccatcgc cgcatgcgtg gaacctttgt ggctcctctg    60
ccgatccata ctgcggaact cctagcagct tgttttgctc gcagccggtc tggagcgaaa  120

<210> SEQ ID NO 197
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 197
gtaaatagac ctattgactg gaaagtatgt caaagaattg tgggtctttt gggctttgct      60 gccccttta cacaatgtgg ctatcctgcc ttgatgcctt tatatgcatg tatacaagct      120

<210> SEQ ID NO 198
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 198
cttatcggca ccgacaactc tgttgtcctc tctcggaaat acacctcatt tccatggctg      60
ctagggtgtg ctgccaactg gatcctgcgc gggacgtcct ttgtctacgt cccgtcggcg      120

<210> SEQ ID NO 199
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 199
ctgaatcccg cggacgaccc gtctcggggc cgtttgggac tctaccgtcc ccttcttcat      60
ctgccgttcc ggccaaccac ggggcgcacc tctctttacg cggtctcccc gtctgtgcct      120

<210> SEQ ID NO 200
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 200
tctcatctgc cgggccgtgt gcacttcgct tcacctctgc acgtcgcatg gaaacctccg      60
tgaacgccca ccaggtcttg cccaaggtct tatataagag gactcttgga ctctcagcga      120

<210> SEQ ID NO 201
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 201
tgtcaacgac cgaccttgag gcatacttca aagactgttt gtttaaggac tgggaggagt      60
tgggggaggt actaggaggc tgtaggcata aattggtctg ttcaccagca ccatgcaact      120

<210> SEQ ID NO 202
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 202
ttttcacctc tgcctaatca tctcatgttc atgtcctact gttcaagcct ccaagctgtg    60
ccttgggtgg ctttggggca tggacattga cccgtataaa gaatttggag cttctgtgga   120

<210> SEQ ID NO 203
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 203
gttactctct tttttgcctt ctgacttctt tccttctatt cgagatctcc tcgacaccgc    60
ctcagctctg tatcgggagg ccttagagtc tccggaacat tgttctcctc accatacagc   120

<210> SEQ ID NO 204
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 204
actcaggcaa gctattctgt gttggggtga gttgatgaat ctggccacct gggtgggaag    60
taatttggaa gacccagcat ccagggaatt agtagtcagc tatgtcaatg ttaatatggg   120

<210> SEQ ID NO 205
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 205
cctaaaaatc agacaactac tgtggtttca catttcctgt cttacttttg gaagagaaac    60
tgttcttgag tatttggtgt cttttggagt gtggattcgc actcctcctg cttacagacc   120

<210> SEQ ID NO 206
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 206
accaaatgcc cctatcttat caacacttcc ggaaactact gttgttagac gacgaggcag    60
gtcccctaga agaagaactc cctcgcctcg cagacgaagg tctcaatcgc cgcgtcgcag   120

<210> SEQ ID NO 207
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 207
aagatctcaa tctcgggaat ctcaatgtta gtatcccttg gactcataag gtgggaaact    60
ttactgggct ttattcttct actgtacctg tctttaatcc tgagtggcaa actccctcct   120

<210> SEQ ID NO 208
<211> LENGTH: 120

```
<212> TYPE: DNA
<213> ORGANISM: Artificial Sequence
<220> FEATURE:
<223> OTHER INFORMATION: Synthetic Polynucleotide

<400> SEQUENCE: 208
caccaagctc tgatagaccc cagagtaagg ggcctatact ttcctgctgg tggctccagt    60
tccggaacag taaaccctgt tccgactact gcctcaccca tatcgtcaat cttctcgagg   120

<210> SEQ ID NO 209
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 209
ctttctcgcc aacttacaag gcctttctgt gtaaacaata tctgaacctt taccccgttg    60
ctcggcaacg gtcaggttta tgccaagtgt ttgctgacgc aaccccccact ggatggggct   120

<210> SEQ ID NO 210
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 210
ggaaggcagg cattctatat aagagagaaa ctacacgcag cgcctcattt tgtgggtcac    60
catattcttg ggaacaagag ctacagcatg ggaggttggt cttccaaacc tcgacaaggc   120

<210> SEQ ID NO 211
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 211
actggatggg gcttggccat aggccatcag cgcatgcgtg gaacctttgt ggctcctctg    60
ccgatccata ctgcggaact catagaagct tgttttgctc gcagccggtc tggagcgaaa   120

<210> SEQ ID NO 212
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 212
ctgaatcccg cggacgaccc gtctcgggac cgtttgggcc tctaccgtcc ccttcttcat    60
ctgccgttcc ggccgaccac ggggcgcacc tctctttacg cggtctcccc gtctgtgcct   120

<210> SEQ ID NO 213
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 213
cactcctacc gcttacagac caccaaatgc ccctatctta tcaacacttc cggaaactac    60
```

```
tgttgttaga cgacgaggca ggtcccctag aagaagaact ccctcgcctc gcagacgaag    120

<210> SEQ ID NO 214
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 214
ctgctaggtt ctatcctaac cataccaaat atttgccctt ggataaaggc attaaacctt     60
attatcctga acatgtagtt aatcattact tcaaaactag gcattattta catactttgg    120

<210> SEQ ID NO 215
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 215
ggaaggctgg cattcggtat aagagagaaa ctacacgcag cgcttcattt tgtgggtcac     60
catattcttg ggaacaagag ctacagcatg ggaggttggt cttccaaacc tcgacaaggc    120
```

PROBE FOR DETECTING HEPATITIS B VIRUS AND USE THEREOF

CROSS-REFERENCE TO RELATED APPLICATION

This application claims priority to and the benefit of Korean Patent Application No. 10-2019-0139264, filed on Nov. 4, 2019, the disclosure of which is incorporated herein by reference in its entirety.

SEQUENCE LISTING

The instant application contains a Sequence Listing which has been submitted in XML format and is hereby incorporated by reference in its entirety. Said XML copy, created on Dec. 28, 2020, is named "ELIP111seq.txt" and is 58.5 kilobytes in size.

BACKGROUND

1. Field of the Invention

The present invention relates to a probe for detecting hepatitis B virus and a method for detecting an insertion site of hepatitis B virus at high efficiency based on the analysis method of next-generation sequencing using the probe.

2. Discussion of Related Art

Hepatitis B virus (HBV) is a disease which is the main cause of liver cancer, and approximately 300 million people worldwide are affected by HBV. Hepatitis B virus (hereinafter, referred to as 'HBV') is a virus belonging to the Hepadnaviridae family and infects only liver cells of humans specifically. Symptoms of hepatitis are fatigue for mild cases, and jaundice may appear in severe cases. In the late stage of the disease, complications of cirrhosis such as, ascites, edema, gastroesophageal variceal bleeding, hepatic encephalopathy, blood coagulation abnormality, and hepatorenal syndrome can appear.

In the case of patients who have been infected in childhood, the period of immune tolerance occurs continuously for 10 to 30 years in which the proliferation of virus occurs but no symptoms of hepatitis appear, but when these healthy carriers reach a certain period (15 to 30 years old), hepatocytes are damaged by the action of the immune system and develop into hepatitis. When e-antigen seroconversion (HBeAg seroconversion) occurs quickly, viral proliferation is suppressed and symptoms of hepatitis do not develop any further, but when the proliferation of virus is not effectively suppressed, and it develops into chronic hepatitis and liver cirrhosis, and in severe cases, it develops into liver cancer.

Hepatitis B virus can be inserted (integration) into the human genome during viral proliferation and life cycle, and although this step is not essential for viral replication, integration of the HBV DNA into a host genome contributes to the occurrence of liver cancer by inducing genomic instability and altering the expression of cancer-related genes. Until recently, the existence of this genomic insertion phenomenon has traditionally been discovered by polymerase chain reaction (PCR), but this method has a limitation in finding all of HBV-inserted molecules in the entire human genome because it biases detection of only the inserted virus localized in the human genome region designated by a specific primer. Therefore, a new method was necessary to investigate HBV insertion in the entire human genome.

Recently, with the introduction of next-generation sequencing (NGS) technology, it is possible to overcome the limitations of traditional PCR-based studies and to attempt non-biased detection of HBV insertion sites across the entire human genome. The present invention provides a method for analyzing HBV insertion sites at high efficiency based on NGS and a probe applied thereto.

SUMMARY OF THE INVENTION

The present invention provides a probe for detecting hepatitis B virus and a method for detecting an insertion site of hepatitis B virus at high efficiency based on the analysis method of next-generation sequencing using the probe.

The present invention provides a probe composition for detecting hepatitis B virus (HBV) consisting of sequences of SEQ ID NO: 1 to SEQ ID NO: 215.

In addition, the present invention may provide a kit for detecting hepatitis B virus (HBV) including the probe composition.

In addition, the present invention may provide a method for detecting hepatitis B virus (HBV), wherein the method is a method for detecting hepatitis B virus (HBV) through next-generation sequencing (NGS), the method including hybridizing a target sample with a probe composition for detecting hepatitis B virus (HBV) consisting of a sequence selected from the group consisting of SEQ ID NO: 1 to SEQ ID NO: 215 to capture a target gene.

In addition, the present invention may provide a method for providing information for the diagnosis of liver cancer using the method.

According to the present invention, a probe may be provided that is capable of confirming an insertion site of HBV in the human genome with a possibility of developing into liver cancer. In addition, by applying the probe to the analysis method of next-generation sequencing, HBV insertion sites in the human genome can be analyzed at low cost and high efficiency.

BRIEF DESCRIPTION OF THE DRAWINGS

The above and other objects, features and advantages of the present invention will become more apparent to those of ordinary skill in the art by describing in detail exemplary embodiments thereof with reference to the accompanying drawings, in which.

DETAILED DESCRIPTION OF EXEMPLARY EMBODIMENTS

Hereinafter, the present invention will be described in detail.

Figure 1:
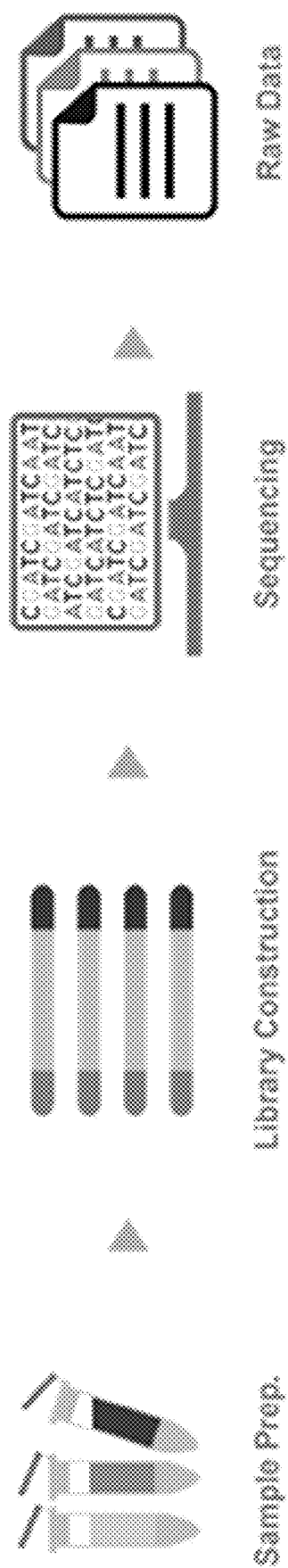
FIG. 1 schematically illustrates a process of analyzing an HBV insertion site.

The present invention may detect an insertion site of hepatitis B virus (HBV) located in the human genome at high efficiency based on next-generation sequencing (NGS). Specifically, in a DNA library constructed from a patient's liver tissue, an HBV sequence may be captured with a probe complementary to the self-constructed HBV. Based on this, HBV and breakpoints of the human genome may be detected (refer to FIG. 1).

As used herein, the term "probe" refers to a nucleic acid fragment corresponding to several bases to several hundred bases for specific binding to DNA or RNA, and afterwards, the presence or absence of specific DNA or RNA may be confirmed by amplification, separation, and detection.

The present invention provides a probe for detecting hepatitis B virus (HBV) consisting of nucleotide sequences of SEQ ID NO: 1 to SEQ ID NO: 215.

The probe may detect an insertion site of hepatitis B virus in the human genome. More specifically, the probe may detect an insertion site of hepatitis B virus (HBV) using the analysis method of next-generation sequencing.

The probe may be applied to the detection of hepatitis B virus of Koreans, and more specifically, it may be applied to the detection of genotype hepatitis C virus.

The length of the probe is 120 nucleotides. When the length of the probe is too short or too long, false hybridization increases and the likelihood of a decrease in specificity increases. In the present invention, hybridization efficiency was maximized by optimizing the length of a probe as above.

In addition, the probe is based on the complete genome sequences of 8 prototypes of hepatitis B virus (HBV) of Koreans, and by allowing each HBV nucleotide sequence to overlap, it is designed to have almost 100% coverage for hepatitis B virus (HBV) of Koreans.

In addition, the present invention provides a composition for detecting hepatitis B virus (HBV), including the probe. The composition may include deoxynucleoside triphosphate (dNTP), heat-resistant polymerase, and a metal ion salt such as magnesium chloride and the like, in addition to the probe.

In addition, the present invention provides a kit for detecting hepatitis B virus (HBV), including the composition.

The kit may include a barcoding primer in which an adapter suitable for the NGS device to be used is combined with a barcode sequence.

In addition, the kit may further include a reagent commonly used in a method for detecting nucleic acid. For example, it may include deoxynucleoside triphosphate (dNTP), heat-resistant polymerase, and a metal ion salt such as magnesium chloride and the like that are required for PCR reaction, and may include dNTP, sequenase, and the like that are required for sequencing. In addition, the kit may take the form of a bottle, a tub, a sachet, an envelope, a tube, an ampoule, and the like, and these may be partially or entirely formed from plastic, glass, paper, foil, wax, and the like. The container may be equipped with a completely or partially removable plug, which is initially part of a container or may be attached to the container by mechanical, adhesive, or other means. The container may be equipped with a stopper that may allow access to the contents by an injection needle. The kit may include an external package, and the external package may include instructions for use of the components.

The present invention provides a method for detecting hepatitis B virus (HBV), wherein the method is a method for detecting hepatitis B virus (HBV) through next-generation sequencing (NGS), the method including hybridizing a target sample with a probe for detecting hepatitis B virus (HBV) composed of a sequence selected from the group consisting of SEQ ID NO: 1 to SEQ ID NO: 215 to capture a target gene.

As used herein, the term "hybridization" means that complementary single-stranded nucleic acids form double-stranded nucleic acids. The degree of complementarity required for hybridization may vary depending on the hybridization conditions, and in particular, if it can be optimized at temperature, it may be preferably optimized to a temperature described in the protocol that can be specified by the probe manufacturer.

As used herein, the term "target gene" refers to a gene sequence to be detected, and it is hybridized with a probe under hybridization, annealing, or amplification conditions.

As used herein, the term "target gene" is not different from the terms used in the present specification such as "target gene", "target gene sequence", or "target sequence", and these terms are used interchangeably in the present specification.

As used herein, a target sample refers to a sample including a gene region to be detected, and it may be collected from at least one selected from the group consisting of tissue, blood, serum, saliva, urine, semen, and body fluid, and specifically, it may be liver tissue derived from a patient.

In addition, the present invention provides a method for detecting hepatitis B virus (HBV), including (a) hybridizing a target sample including a target gene with a probe for detecting hepatitis B virus (HBV) composed of a sequence selected from the group consisting of SEQ ID NO: 1 to SEQ ID NO: 215 to capture a target gene and amplifying to create a library; and (b) sequencing the library to map the produced nucleotide sequence in the human and HBV reference sequences for analysis to confirm an insertion site of hepatitis B virus (HBV) in the human genome.

The hybridizing may be performed at a temperature of 65° C. for 16 hours to 24 hours.

Since it is a temperature and time condition that optimizes the efficiency of probe hybridization, the hybridization efficiency may be lowered when an experiment outside this range is performed.

The target gene may be a hepatitis B virus (HBV) gene of Koreans.

In addition, the present invention may provide a method for providing information for the diagnosis of liver cancer, using the method.

Hereinafter, the present invention will be described in more detail through exemplary embodiments. Objects, features, and advantages of the present invention will be easily understood through the following exemplary embodiments. The present invention is not limited to the exemplary embodiment described herein, and may be embodied in other forms. The exemplary embodiments introduced herein are provided in order to sufficiently convey the spirit of the present invention to those of ordinary skill in the technical field to which the present invention pertains. Therefore, the present invention should not be limited by the following exemplary embodiments.

EXAMPLES

Example 1: Preparation of probe for HBV detection

In order to perform next-generation sequencing analysis for the detection of an HBV insertion site, a probe for HBV capture was prepared based on the following complete genome sequences of 8 representative Korean HBV types. Complementary probes were prepared such that each HBV nucleotide sequence overlapped with each other. The probe was synthesized through the HPLC purification method, and the concentration and purity of the synthesized probe were confirmed using the BioAnalyzer device.

TABLE 1

HBV Prototype

| Target Reference | start | end |
|---|---|---|
| KR184660.1 Hepatitis B virus isolate SS_3_22, complete genome | 1 | 3207 |
| JN315779.1 Hepatitis B virus genotype C2, complete genome | 1 | 3215 |
| GQ872211.1 Hepatitis B virus, complete genome | 1 | 3215 |
| D23680.1 Hepatitis B virus (B4-HBVST1) complete genome sequence | 1 | 3194 |
| AY641559.1 Hepatitis B virus isolate He53, complete genome | 1 | 3215 |
| isolate 36Y18HCC","AB014395.1 Hepatitis B virus genomic DNA, complete sequence | 1 | 3119 |
| isolate 22Y04HCC","AB014381.1 Hepatitis B virus genomic DNA, complete sequence | 1 | 3215 |
| DQ683578.1 Hepatitis B virus from South Korea, complete genome | 1 | 3215 |

(Sequence Information)
The probe targets the following 8 viruses.
complete genome","AY641559.1 Hepatitis B virus isolate He53 (can be found at www.ncbi.nlm.nih.gov as AY641559.1)
complete genome","DQ683578.1 Hepatitis B virus from South Korea (can be found at www.ncbi.nlm.nih.gov as DQ683578.1)
complete genome","GQ872211.1 Hepatitis B virus (can be found at www.ncbi.nlm.nih.gov as GQ872210.1)
complete genome","JN315779.1 Hepatitis B virus genotype C2 (can be found at www.ncbi.nlm.nih.gov as JN315779)
complete genome","KR184660.1 Hepatitis B virus isolate SS 3 22 (can be found at www.ncbi.nlm.nih.gov as KR184660.1)
complete sequence, isolate 22Y04HCC","AB014381.1 Hepatitis B virus genomic DNA (can be found at www.ncbi.nlm.nih.gov as 3582357)
complete sequence, isolate 36Y18HCC","AB014395.1 Hepatitis B virus genomic DNA (can be found at www.ncbi.nlm.nih.gov as 3551389)
D23680.1 Hepatitis B virus (B4-HBVST1) complete genome sequence (can be found at www.ncbi.nlm.nih.gov as D23680.1)

Based on the above contents, it was prepared by Tilling density 1X, Boosting: balanced, probe group size: 25.595 kbp, Total probe: 215. The sequence information of each designed probe was shown in Table 2 below.

TABLE 2

| TargetID | ProbeID | Sequence | SEQ ID NO |
|---|---|---|---|
| KR184660.1 Hepatitis B virus isolate SS_3_22, complete genome | probe_HBV_012017_1 | CTCCACAACATTCCACCAAGCTCTGCT AGATCCCAGAGTGAGGGGCCTATATTT TCCTGCTGGTGGCTCCAGTTCCGAAC AGTAAACCCTGTTCCGACTATTGTCTC ACCCATATCGTC | SEQ ID NO: 1 |
| KR184660.1 Hepatitis B virus isolate SS_3_22, complete genome | probe_HBV_012017_10 | AAGCAGGCCTTCACTTTCTCGCCAACT TACAAGGCCTTTCTGTGTAAACAATAT CTGCACCTTTACCCCGTTGCCCGGCAA CGGTCAGGTCTCTGCCAAGTATTTGCT GACGCAACCCCC | SEQ ID NO: 2 |
| D23680.1 Hepatitis B virus (B4-HBVST1) complete genome sequence | probe_HBV_012017_100 | TTCCTCACATTCATTTACAGGAGGACA TTATTAATAGATGTGAACAATATGTGG GCCCTCTTACAGTTAATGAAAAAAGGA GATTAAAATTAATTATGCCTGCTAGGT TCTATCCTAACC | SEQ ID NO: 3 |
| D23680.1 Hepatitis B virus (B4-HBVST1) complete genome sequence | probe_HBV_012017_101 | TTACCAAATATTTGCCATTGGACAAAG GCATTAAACCATATTATCCTGAACATG CAGTTAATCATTACTTCAAAACTAGGC ATTATTTACATACTCTGTGGAAGGCGG GCATTCTATATA | SEQ ID NO: 4 |
| D23680.1 Hepatitis B virus (B4-HBVST1) complete genome sequence | probe_HBV_012017_102 | AGAGAGAAACTACACGCAGTGCCTCA TTCTGTGGGTCACCATATTCTTGGGAA CAAGAGCTACAGCATGGGAGGTTGGT CTTCCAAACCTCGACAAGGCATGGGA CGAATCTTTCTGTT | SEQ ID NO: 5 |
| D23680.1 Hepatitis B virus (B4-HBVST1) complete genome sequence | probe_HBV_012017_103 | CCCAATCCTCTGGGATTCTTTCCCGATC ACCAGTTGGACCCTGCATTCGGAGCCA ACTCAAACAATCCAGATTGGGACTTCA ACCCCAACAAGGATCATTGGCCAGAG GCAAATCAGGTA | SEQ ID NO: 6 |
| D23680.1 Hepatitis B virus (B4-HBVST1) complete genome sequence | probe_HBV_012017_104 | GGAGCGGGAGCATTCGGGCCAGGGTT CACCCCACCACACGGCGGTCTTTTGGG GTGGAGCCCGCAGGCTCAGGGCATATT GACAACCGTGCCAGTAGCACCTCCTCC TGCCTCCACCAAT | SEQ ID NO: 7 |
| AY641559.1 Hepatitis B virus isolate He53, complete genome | probe_HBV_012017_105 | CTCCACCACATTCCACCAAGCTCTACT AGATCCCAGAGTGAGGGGCCTATATTT TCCTGCTGGTGGCTCCAGTTCCGAAC AGTAAACCCTGTTCCGACTACTGCCTC ACCCATATCGTC | SEQ ID NO: 8 |

TABLE 2-continued

| TargetID | ProbeID | Sequence | SEQ ID NO |
|---|---|---|---|
| AY641559.1 Hepatitis B virus isolate He53, complete genome | probe_HBV_012017_106 | AATCTTCTCGAGGACTGGGGACCCTGC ACCGAACATGGAGAGCACAACATCAG GATTCCTAGGACCCCTGCTCGTGTTAC AGGCGGGGTTTTTCTTGTTGACAAGAA TCCTCACAATACC | SEQ ID NO: 9 |
| AY641559.1 Hepatitis B virus isolate He53, complete genome | probe_HBV_012017_107 | ACAGAGTCTAGACTCGTGGTGGACTTC TCTCAATTTTCTAGGGGGAGCACCCAC GTGTCCTGGCCAAAATTCGCAGTCCCC AACCTCCAATCACTCACCAACCTCTTG TCCTCCAATTTG | SEQ ID NO: 10 |
| AY641559.1 Hepatitis B virus isolate He53, complete genome | probe_HBV_012017_108 | TCCTGGCTATCGCTGGATGTGTCTGCG GCGTTTTATCATATTCCTCTTCATCCTG CTGCTATGCCTCATCTTCTTGTTGGTTC TTCTGGACTACCAAGGTATGTTGCCCG TTTGTCCTCT | SEQ ID NO: 11 |
| AY641559.1 Hepatitis B virus isolate He53, complete genome | probe_HBV_012017_109 | ACTTCCAGGAACATCAACTACCAGCAC GGGACCATGCAAGACCTGCACGATTCC TGCTCAAGGAACCTCTATGTTTCCCTCT TGTTGCTGTACAAAACCTTCGGACGGA AATTGCACTTG | SEQ ID NO: 12 |
| KR184660.1 Hepatitis B virus isolate SS_3_22, complete genome | probe_HBV_012017_11 | ACTGGATGGGGCTTGGCCATAGGCCAT CGGCGCATGCGTGGAACCTTTGTGGCT CCTCTGCCGATCCATACTGCGGAACTC CTAGCAGCTTGTTTTGCTCGCAGCCGG TCTGGAGCGAAA | SEQ ID NO: 13 |
| AY641559.1 Hepatitis B virus isolate He53, complete genome | probe_HBV_012017_110 | TATTCCCATCCCATCATCCTGGGCTTTC GCAAAATTCCTATGGGAGTGGGCCTCA GTCCGTTTCTCCTGGCTCAATTTACTAG TGCCATTTGTTCAGTGGTTCGCAGGGC TTTCCCCCAC | SEQ ID NO: 14 |
| AY641559.1 Hepatitis B virus isolate He53, complete genome | probe_HBV_012017_111 | TGTTTGGCTTTCAGTTATATGGATGAT GTGGTATTGGGGGCCAAGTCTGTACAA CATCTTGAGGCCCTTTATACCTCTATTA CCAATTTTCTTGTGTCTTTGGGTATACA TTTGAACCCT | SEQ ID NO: 15 |
| AY641559.1 Hepatitis B virus isolate He53, complete genome | probe_HBV_012017_112 | AATAAAACCAAACGTTGGGGCTACTCC CTTAACTTCATGGGATATGTAATTGGA AGTTGGGGTACTTTACCACAGGAACAT ATTGTACAAAAAATTAAGCAATGTTTT CGGAAACTGCCT | SEQ ID NO: 16 |
| AY641559.1 Hepatitis B virus isolate He53, complete genome | probe_HBV_012017_113 | GTCAATAGACCTATTGATTGGAAAGTA TGTCAAAGAATTGTAGGTCTTTTGGGA TTTGCTGCCCCTTTTACACAATGTGGCT ATCCTGCTTTGATGCCTTTATATGCATG TATACAAGCT | SEQ ID NO: 17 |
| AY641559.1 Hepatitis B virus isolate He53, complete genome | probe_HBV_012017_114 | AAGCAGGCTTTCACTTTCTCGTCAACT TACAAGGCCTTTCTGTGTAAACAATAT CTGCACCTTTACCCCGTTGCCCGGCAA CGGTCAGGTCTCTGCCAAGTGTTTGCT GACGCAACCCCC | SEQ ID NO: 18 |
| AY641559.1 Hepatitis B virus isolate He53, complete genome | probe_HBV_012017_115 | ACTGGATGGGGCTTGGCCATAGGCCAT CGGCGCATGCGTGGAACCTTTGTGGCT CCTCTGCCGATCCATACTGCGGAACTC CTAGCAGCTTGTTTTGCTCGCAGCCGG TCTGGAGCAAAC | SEQ ID NO: 19 |
| AY641559.1 Hepatitis B virus isolate He53, complete genome | probe_HBV_012017_116 | CTTATCGGGACTGACAACTCTGTTGTC CTCTCTCGGAAATACACCTCCTTCCCA TGGCTGCTCGGGTGTGCTGCCAACTGG ATCCTGCGCGGGACGTCCTTTGTCTAC GTCCCGTCGGCG | SEQ ID NO: 20 |
| AY641559.1 Hepatitis B virus isolate He53, complete genome | probe_HBV_012017_117 | CTGAATCCCGCGGACGACCCGTCTCGG GGCCGTTTGGGCCTCTACCGTCCCCTT CTTCATCTGCCGTTCCGGCCGACCACG GGGCGCACCTCTCTTTACGCGGTCTCC CCGTCTGTGCCT | SEQ ID NO: 21 |

TABLE 2-continued

| TargetID | ProbeID | Sequence | SEQ ID NO |
|---|---|---|---|
| AY641559.1 Hepatitis B virus isolate He53, complete genome | probe_HBV_012017_118 | TCTCATCTGCCGGTCCGTGTGCACTTC GCTTCACCTCTGCACGTCGCATGGAAA CCACCGTGAACGCCCATCCGGTCTTGC CCAAGGTCTTATATAAGAGGACTCTTG GACTCTCAGCAA | SEQ ID NO: 22 |
| AY641559.1 Hepatitis B virus isolate He53, complete genome | probe_HBV_012017_119 | TGTCAACGACCGACCTTGAGGCATACT TCAAAGACTGTTTGTTTAAAGACTGGG AGGAGTTGGGGGAGGAGAATAGGTTA ATGATCTTTGTACTAGGAGGCTGTAGG CATAAATTGGTCT | SEQ ID NO: 23 |
| KR184660.1 Hepatitis B virus isolate SS_3_22, complete genome | probe_HBV_012017_12 | CTCATCGGGACTGACAACTCGGTTGTT CTCTCTCGGAAATACACCTCATTCCCA TGGCTGCTCGGGTGTGCTGCCAACTGG ATCCTGCGCGGGACGTCCTTTGTTTAC GTCCCGTCGGCG | SEQ ID NO: 24 |
| AY641559.1 Hepatitis B virus isolate He53, complete genome | probe_HBV_012017_120 | GTTCACCAGCACCATGCAACTTTTTCA CCTCTGCCTAATCATCTCTTGTTCATGT CCTACTGTTCAAGCCTCCAAGCTGTGC CTTGGGTGGCTTTAGGACATGGACATT GACCCGTATAA | SEQ ID NO: 25 |
| AY641559.1 Hepatitis B virus isolate He53, complete genome | probe_HBV_012017_121 | AGAATTTGGAGCTTCTGTGGAGTTGCT CTCTTTTTTGCCTTCTGACTTCTTTCCTT CTATTCGAGATCCTCGACACCGCCT CTGCTCTCTATCGGGAGGCCTTAGAGT CTCCGGAACA | SEQ ID NO: 26 |
| AY641559.1 Hepatitis B virus isolate He53, complete genome | probe_HBV_012017_122 | TTGTTCACCTCACCATACAGCACTCAG GCAAGCTATTCTGTGTTGGGGTGAGTT GATGAACCTGGCCACCTGGGTGGGAA GTAATTTGGAAGATCCTGCATCCAGGG AATTAGTAGTCAG | SEQ ID NO: 27 |
| AY641559.1 Hepatitis B virus isolate He53, complete genome | probe_HBV_012017_123 | CTATGTCAATGTTAATATGGGCCTAAA ACTCAGACAAATATTGTGGTTTCACAT TTCCTGTCTTACTTTTGGAAGAGAAAC CGTTCTTGAGTATTTGGTGTCTTTTGGA GTGTGGATTCG | SEQ ID NO: 28 |
| AY641559.1 Hepatitis B virus isolate He53, complete genome | probe_HBV_012017_124 | CACTCCTACCGCTTACAGACCACCAAA TGCCCCTATCTTATCAACACTTCCGGA AACTACTGTTGTTAGACGACGAGGCAG GACCCCTAGAAGAAGAACTCCCTCGCC TCGCAGACGAAG | SEQ ID NO: 29 |
| AY641559.1 Hepatitis B virus isolate He53, complete genome | probe_HBV_012017_125 | ATCTCAATCGCCGCGTCGCAGAAGATC TCAATCTCGGGAATCTCAATGTTAGTA TCCCCTGGACTCACAAGGTGGGAAATT TTACTGGGCTTTACTCGTCTACTGTACC TATCTTTAATC | SEQ ID NO: 30 |
| AY641559.1 Hepatitis B virus isolate He53, complete genome | probe_HBV_012017_126 | CTGATTGGCAAACTCCCTCCTTTCCTA ACATTCATTTACAGGAGGACATTATTG ATAGATGTCAACAATATGTAGGCCCTC TTACAGTTAATGAAAAAAGGAGATTA AAATTAATTATGC | SEQ ID NO: 31 |
| AY641559.1 Hepatitis B virus isolate He53, complete genome | probe_HBV_012017_127 | CTGCTAGGTTTTATCCTAACCTTACCA AATATTTGCCCTTGGATAAAGGCATTA AACCTTATTATCCTGAACATGCAGTTA ATCATTACTTCCAAACTAGGCATTATT TACATACTCTGT | SEQ ID NO: 32 |
| AY641559.1 Hepatitis B virus isolate He53, complete genome | probe_HBV_012017_128 | GGAAGGCTGGCATTCTATATAAGAGA GAAACTACACGCAGCGCTTCATTTTGT GGGTCACCATATTCTTGGGAACAAGAG CTACAGCATGGGAGGTTGGTCTTCCAA ACCTCGACAAGGC | SEQ ID NO: 33 |
| AY641559.1 Hepatitis B virus isolate He53, complete genome | probe_HBV_012017_129 | ATGGGGACGAATCTTTCTGTTCCCAAT CCTCTGGGATTCTTTCCCGATCACCAG TTGGACCCTGCGTTCGGAGCCAACTCA AACAATCCAGATTGGGACTTCAACCCC AACAAGGATCAC | SEQ ID NO: 34 |

TABLE 2-continued

| TargetID | ProbeID | Sequence | SEQ ID NO |
|---|---|---|---|
| KR184660.1 Hepatitis B virus isolate SS_3_22, complete genome | probe_HBV_012017_13 | CTGAATCCCGCGGACGACCCGTCTCGC GGCCGTTTGGGCCTCTACCGTCCCCTT CTTCATCTGCCGTTCCGGCCGACCACG GGGCGCACCTCTCTTTACGCGGTCTCC CCGTCTGTGCCT | SEQ ID NO: 35 |
| AY641559.1 Hepatitis B virus isolate He53, complete genome | probe_HBV_012017_130 | TGGCCAGAGGCAAATCAGGTCGGAGT GGGAGCATTCGGGCCAGGGTTCACCCC ACCACACGGCGGTCTTTTGGGGTGGAG CCCTCAGGCTCGGGGCATAGTGACACC AGTGCCAGCAGCG | SEQ ID NO: 36 |
| isolate 36Y18HCC","AB01439 5.1 Hepatitis B virus genomic DNA, complete sequence | probe_HBV_012017_132 | ACTGGGGACCCTGCACCGAACATGGA GAACACAACATCAGGATTCCTAGGACC CCTGCTCGTGTTACAGGCGGGGTTTTT CTTGTTGACAAGAATCCTCACAATACC ACAGAGTCTAGAC | SEQ ID NO: 37 |
| isolate 36Y18HCC","AB01439 5.1 Hepatitis B virus genomic DNA,complete sequence | probe_HBV_012017_133 | TCGTGGTGGACTTCTCTCAATTTTCTAG GGGGAACACCCACGTGTCCTGGCCAA AATTCGCAGTCCCCAACCTCCAATCAC TCACCAACCTCTTGTCCTCCAATTTGTC CTGGCTATCGC | SEQ ID NO: 38 |
| isolate 36Y18HCC","AB01439 5.1 Hepatitis B virus genomic DNA,complete sequence | probe_HBV_012017_134 | TGGATGTGTCTGCGGCGTTTTATCATA TTCCTCTTCATCCTGCTGCTATGCCTCA TCTTCTTGTTGGTTCTTCTGGACTACCA AGGTATGTTGCCCGTTTGTCCTCTACTT CCAGGAACA | SEQ ID NO: 39 |
| isolate 36Y18HCC","AB01439 5.1 Hepatitis B virus genomic DNA,complete sequence | probe_HBV_012017_135 | TCAACTACCAGCACGGGACCATGCAA GACCTGCACGATTCCTGCTCAAGGCAC CTCTATGTTTCCCTCTTGTTGCTGTACA AAACCTTCGGATGGAAACTGCACTTGT ATTCCCATCCCA | SEQ ID NO: 40 |
| isolate 36Y18HCC","AB01439 5.1 Hepatitis B virus genomic DNA,complete sequence | probe_HBV_012017_136 | TCATCCTGGGTTTTCGCAAGATTCCTAT GGGAGTGGGCCTCAGTCCGTTTCTCCT GGCTCAGTTTACTAGTGCCATTTGTTC AGTGGTTCGTAGGGCTTTCCCCCACTG TTTGGCTTTCA | SEQ ID NO: 41 |
| isolate 36Y18HCC","AB01439 5.1 Hepatitis B virus genomic DNA,complete sequence | probe_HBV_012017_137 | GTTATATGGATGATATAGTATTGGGGG CCAAGTCTGTACAACATCTTGAGTCCC TTTATACCGCCATTACCAATTTTCTTTT GTCTTTGGGTATACATTTGAACCCTAA TAAAACCAAAC | SEQ ID NO: 42 |
| isolate 36Y18HCC","AB01439 5.1 Hepatitis B virus genomic DNA,complete sequence | probe_HBV_012017_138 | GTTGGGGCTACTCCCTGAACTTCATGG GATATGTAATTGGAAGTTGGGGTACTT TACCGCAAGACCATATTGTACTAAAAC TCAAGCAATGTTTTCGAAAACTGCCTG TAAATAGACCTA | SEQ ID NO: 43 |
| isolate 36Y18HCC","AB01439 5.1 Hepatitis B virus genomic DNA,complete sequence | probe_HBV_012017_139 | TTGATTGGAAAGTATGTCAGAGAATTG TGGGTCTTTTGGGCTTTGCTGCCCCTTT TACACAATGTGGCTATCCTGCCTTAAT GCCTTTATATGCATGTATACAATCTAA GCAGGCTTTCA | SEQ ID NO: 44 |
| KR184660.1 Hepatitis B virus isolate SS_3_22, complete genome | probe_HBV_012017_14 | TCTCATCTGCCGGACCGTGTGCACTTC GCTTCACCTCTGCACGTCGCATGGAGA CCACCGTGAACGCCCATCAGGTCTTGC CCAAGGTCTTACATAAGAGGACTCTTG GACTCTCAGCAA | SEQ ID NO: 45 |
| isolate 36Y18HCC","AB01439 5.1 Hepatitis B virus genomic DNA,complete sequence | probe_HBV_012017_141 | TGGCTATTGCCATCAGCGCATGCGTG GAACCTTTGTGGCTCCTCTGCCGATCC ATACTGCGGAACTCCTAGCAGCTTGTT TTGCTCGCAGCCGGTCTGGAGCGAAAC TGATCGGAACGG | SEQ ID NO: 46 |
| isolate 36Y18HCC","AB01439 5.1 Hepatitis B virus genomic DNA,complete sequence | probe_HBV_012017_142 | ACAACTCTGTTGTTCTCTCTCGGAAAT ACACCTCCTTTCCATGGCTGCTAGGGT GTGCTGCCAACTGGATCCTGCGCGGGA CGTCCTTTGTTTACGTCCCGTCGGCGCT GAATCCCGCGG | SEQ ID NO: 47 |

TABLE 2-continued

| TargetID | ProbeID | Sequence | SEQ ID NO |
|---|---|---|---|
| isolate 36Y18HCC","AB01439 5.1 Hepatitis B virus genomic DNA,complete sequence | probe_HBV_012017_143 | ACGACCCATCTCGGGGCCGTTTGGGTC TCTACCGTCCCCTTCTTCATCTGCCGTT CCGGCCGACCACGGGGCGCACCTCTCT TTACGCGGTCTCCCCGTCTGTGCCTTCT CATCTGCCGG | SEQ ID NO: 48 |
| isolate 36Y18HCC","AB01439 5.1 Hepatitis B virus genomic DNA,complete sequence | probe_HBV_012017_144 | ACCGTGTGCACTTCGCTTCACCTCTGC ACGTCGCATGGAGACCACCGTGAACG CCCACCAGGTCTTGCCCAAGGTCTTAT ATAAGAGGACTCTTGGACTCTCAGCAA TGTCAACGACCGA | SEQ ID NO: 49 |
| isolate 36Y18HCC","AB01439 5.1 Hepatitis B virus genomic DNA,complete sequence | probe_HBV_012017_145 | CCTTGAGGCATACTTCAAAGACTGTTT GTTTAAGGACTGGGAGGAGTTGGGGG AGGAGTTTAGGTTAATGATCTTTGTAC TAGGAGGCTGTAGGCATAAATTGGTCT GTTCACCAGCACC | SEQ ID NO: 50 |
| isolate 36Y18HCC","AB01439 5.1 Hepatitis B virus genomic DNA,complete sequence | probe_HBV_012017_146 | ATGCAACTTTTTCACCTCTGCCTAATCA TCTCATGTTCATGTCCTACTGTTCAAGC CTCCAAGCTGTGCCTTGGGTGGCTTTG GGGCATGGACATTGACCCGTATAAAG AATTTGGAGCT | SEQ ID NO: 51 |
| isolate 36Y18HCC","AB01439 5.1 Hepatitis B virus genomic DNA,complete sequence | probe_HBV_012017_147 | TCTGTGGAGTTACTCTCTTTTTTGCCTT CTGACTTCTTTCCTTCTATTCGAGATCT CCTCGACACCGCCTCTGCTCTGTATCG GGAGGCCTTAGAGTCTCCGGAACATTG TTCACCTCAC | SEQ ID NO: 52 |
| isolate 36Y18HCC","AB01439 5.1 Hepatitis B virus genomic DNA,complete sequence | probe_HBV_012017_148 | CATACAGCAATCAGGCAAGCTATTCTG TGTTGGGGTGAGTTGATGAATCTGGCC ACCTGGGTGGGAAGTAATTTGGAAGA CCCAGCATCCAGGGAATTAGTAGTCAG CTATGTCAATGTT | SEQ ID NO: 53 |
| isolate 36Y18HCC","AB01439 5.1 Hepatitis B virus genomic DNA,complete sequence | probe_HBV_012017_149 | AATATGGGCCTAAAAATCAGACAACT ACTGTGGTTTCACATTTCCTGTCTTACT TTTGGAAGAGAAACTGTTCTTGAGTAT TTGGTGTCTTTTGGAGTGTGGATTCGC ACTCCTCCCGCT | SEQ ID NO: 54 |
| KR184660.1 Hepatitis B virus isolate SS_3_22, complete genome | probe_HBV_012017_15 | TGTCAACGTCCGACCTTGAGGCATACT TCAAAGACTGTTTGTTTAAGGACTGGG AGGAGTTGGGGGAGGAGATTAGGTTA AAGGTCTGGAGGCTGTAGGCATAAATT GGTCTGTTCACCA | SEQ ID NO: 55 |
| isolate 36Y18HCC","AB01439 5.1 Hepatitis B virus genomic DNA,complete sequence | probe_HBV_012017_150 | TACAGACCACCAAATGCCCCTATCTTA TCAACACTTCCGGAAACTACTGTTGTT AGACGACGAGGCAGGTCCCCTAGAAG AAGAACTCCCTCGCCTCGCAGACGAAG GTCTCAATCGCCG | SEQ ID NO: 56 |
| isolate 36Y18HCC","AB01439 5.1 Hepatitis B virus genomic DNA,complete sequence | probe_HBV_012017_151 | CGTCGCAGAAGATCTCAATCTCGGGAA TCTCAATGTTAGTATCCCTTGGACTCAT AAGGTGGGAAACTTTACTGGGCTTTAT TCTTCTACTGTACCTGTCTTTAATCCTG AGTGGCAAAC | SEQ ID NO: 57 |
| isolate 36Y18HCC","AB01439 5.1 Hepatitis B virus genomic DNA,complete sequence | probe_HBV_012017_152 | TCCCTCCTTTCCTCACATTCATTTGCAG GAGGACATTATTAATAGATGTCAACAA TATGTGGGCCCTCTTACAGTTAATGAA AAAAGGAGATTAAAATTAATTATGCCT GCTAGGTTCTA | SEQ ID NO: 58 |
| isolate 36Y18HCC","AB01439 5.1 Hepatitis B virus genomic DNA,complete sequence | probe_HBV_012017_153 | TCCTAACCTTACCAAATATTTGCCCTTG GACAAAGGCATTAAACCATATTATCCT GAACATGCAGTTCATCATTACTTCAAA ACTAGGCATTATTTACATACTCTGTGG AAGGCTGGCAT | SEQ ID NO: 59 |
| isolate 36Y18HCC","AB01439 5.1 Hepatitis B virus genomic DNA,complete sequence | probe_HBV_012017_154 | TCTATATAAGAGAGAAACTACACGCA GCGCCTCATTTTGTGGGTCACCATATT CTTGGGAACAAGAGCTACAGCAAACC TCGACAAGGCATGGGGACAAATCTTTC TGTTCCCAATCCTC | SEQ ID NO: 60 |

TABLE 2-continued

| TargetID | ProbeID | Sequence | SEQ ID NO |
|---|---|---|---|
| isolate 36Y18HCC","AB014395.1 Hepatitis B virus genomic DNA,complete sequence | probe_HBV_012017_155 | TGGGATTCTTTCCCGATCACCAGTTGG ACCCTGCGTTCGGAGCCAACTCAAACA ATCCAGATTGGGACTTCAACCCCAACA AGGATCACTGGCCAGAGGCAAATCAG GTAGGAGCGGGAG | SEQ ID NO: 61 |
| isolate 22Y04HCC","AB014381.1 Hepatitis B virus genomic DNA,complete sequence | probe_HBV_012017_156 | CTCCACCACATTCCACCAAGCTCTGCT ACACCCCAGAGTAAGGGGCCTATACTT TCCTGCTGGTGGCTCCAGTTCCGGAAC AGTAAACCCTGTTCCGACTACTGCCTC TCCCATATCGTC | SEQ ID NO: 62 |
| isolate 22Y04HCC","AB014381.1 Hepatitis B virus genomic DNA,complete sequence | probe_HBV_012017_157 | AATCTTCTCGAGGACTGGGGACCCTGC ACCGAACATGGAGAACACAACATCAG GATTCCTAGGACCCCTGCTCGTGTTAC AGGCGGGGTTTTTCTTGTTGACAAGAA TCCTCACAATACC | SEQ ID NO: 63 |
| isolate 22Y04HCC","AB014381.1 Hepatitis B virus genomic DNA,complete sequence | probe_HBV_012017_158 | ACAGAGTCTAGACTCGTGGTGGACTTC TCTCAATTTTCTAGGGGGAGCACCCAC GTGTCCTGGCCAAAATTCGCAGTCCCC AACCTCCAATCACTCACCAACCTCTTG TCCTCCAATTTG | SEQ ID NO: 64 |
| isolate 22Y04HCC","AB014381.1 Hepatitis B virus genomic DNA,complete sequence | probe_HBV_012017_159 | TCCTGGCTATCGCTGGATGTGTCTGCG GCGTTTTATCATATTCCTCTTCATCCTG CTGCTATGCCTCATCTTCTTGTTGGTTC TTCTGGACTACCAAGGTATGTTGCCCG TTTGTCCTCT | SEQ ID NO: 65 |
| KR184660.1 Hepatitis B virus isolate SS_3_22, complete genome | probe_HBV_012017_16 | GCACCATGCAACTTTTTCACCTCTGCCT AATCATCTCATGTTCATGTCCTACTGTT CAAGCCTCCAAGCTGTGCCTTGGGTGG CTTTGGGGCATGGACATTGACCCGTAT AAAGAATTTG | SEQ ID NO: 66 |
| isolate 22Y04HCC","AB014381.1 Hepatitis B virus genomic DNA,complete sequence | probe_HBV_012017_160 | ACTTCCAGGAACATCAACTACCAGCAC GGGACCATGCAAGACCTGCACGATTCC TGCTCAAGGCACCTCTATGTTTCCCTCT TGTTGCTGTACAAAACCTTCGGACGGA AACTGCACTTG | SEQ ID NO: 67 |
| isolate 22Y04HCC","AB014381.1 Hepatitis B virus genomic DNA,complete sequence | probe_HBV_012017_161 | TATTCCCATCCCATCATCCTGGGCTTTC GCAAGATTCCTATGGGAGTGGGCCTCA GTCCGTTTCTCCTGGCTCAGTTTACTAG TGCCATTTGTTCAGTGGTTCGTAGGGC TTTCCCCCAC | SEQ ID NO: 68 |
| isolate 22Y04HCC","AB014381.1 Hepatitis B virus genomic DNA,complete sequence | probe_HBV_012017_162 | TGTTTGGCTTTCAGTTATATGGATGAT GTGGTATTGGGGGCCAAGTCTGTACAA CATCTTGAGTCCCTTTTTACCGCTGTTA CCAATTTTCTTTTGTCTTTGGGTATACA TTTGAACCCT | SEQ ID NO: 69 |
| isolate 22Y04HCC","AB014381.1 Hepatitis B virus genomic DNA,complete sequence | probe_HBV_012017_163 | AATAAAACCAAACGTTGGGGTTACTCC CTTAACTTCATGGGATATGTAATTGGA AGTTGGGGTACTTTACCGCAAGACCAT ATTGTACTAAAAATCAAGCAATGTTTT CGAAAACTGCCT | SEQ ID NO: 70 |
| isolate 22Y04HCC","AB014381.1 Hepatitis B virus genomic DNA,complete sequence | probe_HBV_012017_164 | GTAAATAGACCTATTGATTGGAAAGTA TGTCAGAGAATTGTGGGTCTTTTGGGC TTTGCTGCCCCTTTTACACAATGTGGCT ATCCTGCCTTAATGCCTTTATATGCATG TATACAATCT | SEQ ID NO: 71 |
| isolate 22Y04HCC","AB014381.1 Hepatitis B virus genomic DNA,complete sequence | probe_HBV_012017_165 | AAGCAGGCTTTCACTTTCTCGCCAACT TACAAGGCCTTTCTGTGTAAACAATAT CTGAACCTTTACCCCGTTGCCCGGCAA CGGTCAGGTCTCTGCCAAGTGTTTGCT GACGCAACCCCC | SEQ ID NO: 72 |
| isolate 22Y04HCC","AB014381.1 Hepatitis B virus genomic DNA,complete sequence | probe_HBV_012017_166 | ACTGGATGGGGCTTGGCTATTGGCCAT CGCCGCATGCGTGGAACCTTTGTGGCT CCTCTGCCGATCCATACTGCGGAACTC CTAGCAGCTTGTTTTGCTCGCAGCCGG TCTGGAGCGAAA | SEQ ID NO: 73 |

TABLE 2-continued

| TargetID | ProbeID | Sequence | SEQ ID NO |
|---|---|---|---|
| isolate 22Y04HCC","AB01438 1.1 Hepatitis B virus genomic DNA, complete sequence | probe_HBV_012017_167 | CTGATCGGAACGGACAACTCTGTTGTT CTCTCTCGGAAATACACCTCCTTTCCAT GGCTGCTAGGGTGTGCTGCCAACTGGA TCCTGCGCGGGACGTCCTTTGTTTACG TCCCGTCGGCG | SEQ ID NO: 74 |
| isolate 22Y04HCC","AB01438 1.1 Hepatitis B virus genomic DNA, complete sequence | probe_HBV_012017_168 | CTGAATCCCGCGGACGACCCATCTCGG GGCCGTTTGGGTCTCTACCGTCCCCTTC TTCATCTGCCGTTCCGGCCGACCACGG GGCGCACCTCTCTTTACGCGGTCTCCC CGTCTGTGCCT | SEQ ID NO: 75 |
| isolate 22Y04HCC","AB01438 1.1 Hepatitis B virus genomic DNA, complete sequence | probe_HBV_012017_169 | TCTCATCTGCCGGACCGTGTGCACTTC GCTTCACCTCTGCACGTCGCATGGAGA CCACCGTGAACGCCCACCAGGTCTTGC CCAAGGTCTTATATAAGAGGACTCTTG GACTCTCAGCAA | SEQ ID NO: 76 |
| KR184660.1 Hepatitis B virus isolate SS_3_22, complete genome | probe_HBV_012017_17 | GAGCTTCTGTGGAGTTACTCTCTTTTTT GCCTTCTGACTTCTTTCCTTCCATTCGA GATCTCCTCGACACCGCCTCTGCTCTG TATCGGGAGGCCTTAGAGTCTCCGGAA CATTGTTCAC | SEQ ID NO: 77 |
| isolate 22Y04HCC","AB01438 1.1 Hepatitis B virus genomic DNA, complete sequence | probe_HBV_012017_170 | TGTCAACGACCGACCTTGAGGCATACT TCAAAGACTGTTTGTTTAAGGACTGGG AGGAGTTGGGGGAGGAGATTAGGTTA ATGATCTTTGTACTAGGAGGCTGTAGG CATAAATTGGTCT | SEQ ID NO: 78 |
| isolate 22Y04HCC","AB01438 1.1 Hepatitis B virus genomic DNA, complete sequence | probe_HBV_012017_171 | GTTCACCAGCACCATGCAACTTTTTCA CCTCTGCCTAATCATCTCATGTTCATGT CCTACTGTTCAAGCCTCCAAGCTGTGC CTTGGGTGGCTTTAGGACATGGACATT GACCCATATAA | SEQ ID NO: 79 |
| isolate 22Y04HCC","AB01438 1.1 Hepatitis B virus genomic DNA, complete sequence | probe_HBV_012017_172 | AGAATTTGGAGCTTCTGTGGAGTTACT CTCTTTTTTTGCCTTCTGACTTTTTTCCTT CTATTCGAGATCTCCTCGACACCGCCT CTGCTCTGTATCGGGAGGCCTTAGAGT CTCCGGAACA | SEQ ID NO: 80 |
| isolate 22Y04HCC","AB01438 1.1 Hepatitis B virus genomic DNA, complete sequence | probe_HBV_012017_173 | TTGTTCACCTCACCATACAGCACTCAG ACAAGCATTCTGTGTTGGGGTGAGTT GATGAATCTGGCCACCTGGGTGGGAA GTAAATTTGGAAGACCCAGCATCCAGGG AATTAGTAGTCAG | SEQ ID NO: 81 |
| isolate 22Y04HCC","AB01438 1.1 Hepatitis B virus genomic DNA, complete sequence | probe_HBV_012017_174 | CTATGTCAATGTTAATATGGGCCTAAA AATCAGACAACTACTGTGGTTTCACAT TTCCTGTCTTACTTTTGGAAGAGAAAC TGTTCTTGAGTATTTGGTGTCTTTTGGA GTGTGGATTCG | SEQ ID NO: 82 |
| isolate 22Y04HCC","AB01438 1.1 Hepatitis B virus genomic DNA, complete sequence | probe_HBV_012017_175 | CACTCCTCCTGCTTACAGACCATCAAA TGCCCCTATCTTATCAACACTTCCGGA AACTACTGTTGTTAGACGACGAGGCAG GTCCCCTAGAAGAAGAACTCCCTCGCC TCGCAGACGAAG | SEQ ID NO: 83 |
| isolate 22Y04HCC","AB01438 1.1 Hepatitis B virus genomic DNA, complete sequence | probe_HBV_012017_176 | GTCTCAATCGCCGCGTCGCAGAAGATC TCAATCTCGGGAACCTCAATGTTAGTA TCCCTTGGACTCATAAGGTGGGAAACT TTACTGGGCTTTATTCTTCTACTGTACC TGTCTTTAATC | SEQ ID NO: 84 |
| isolate 22Y04HCC","AB01438 1.1 Hepatitis B virus genomic DNA, complete sequence | probe_HBV_012017_177 | CTGAGTGGCAAACTCCCTCTTTTCCTC ATATTCATTTGCAGGAGGACATTATTA ATAGATGTCAACAATATGTGGGCCCTC TTACAGTTAATGAAAAAAGGAGATTA AAATTAATTATGC | SEQ ID NO: 85 |
| isolate 22Y04HCC","AB01438 1.1 Hepatitis B virus genomic DNA, complete sequence | probe_HBV_012017_178 | CTGCTAGGTTCTATCCTAACCTTACCA AATATTTGCCCTTGGACAAAGGCATTA AACCATATTATCCGGAACATGCAGTTA ATCATTACTTCAAAACTAGGCATTATT TACATACTCTGT | SEQ ID NO: 86 |

TABLE 2-continued

| TargetID | ProbeID | Sequence | SEQ ID NO |
|---|---|---|---|
| KR184660.1 Hepatitis B virus isolate SS_3_22, complete genome | probe_HBV_012017_18 | CTCACCATACAGCACTCAGGCAAGCTA TTCTCTGTTGGGGTGAGTTGATGAATC TGGCCACCTGGGTGGGAAGTAATTTGG AAGACCCAGCATCCAGGGATTTAGTAG TCAGCTATGTCA | SEQ ID NO: 87 |
| isolate 22Y04HCC","AB01438 1.1 Hepatitis B virus genomic DNA,complete sequence | probe_HBV_012017_180 | ATGGGGACAAATCTTTCTGTTCCCAAT CCTCTGGGATTCTTTCCCGATCACCAG TTGGACCCTGCGTTCGGAGCCAACTCA AACAATCCAGATTGGGACTTCAACCCC AACAAGGATCAC | SEQ ID NO: 88 |
| isolate 22Y04HCC","AB01438 1.1 Hepatitis B virus genomic DNA,complete sequence | probe_HBV_012017_181 | TGGCCAGAGGCAAATCAGGTAGGAGC GGGAGCATTCGGGCCAGGGTTCACCCC ACCACACGGCGGTCTTTTGGGGTGGAG CCCTCAGGCTCAGGGCACATTGACAAC AGTGCCAGTAGCA | SEQ ID NO: 89 |
| DQ683578.1 Hepatitis B virus from South Korea, complete genome | probe_HBV_012017_182 | CTCCACAACATTCCACCAAGCTCTGCT AGATCCCAGAGTGAGGGGCCTATATTT TCCTGCTGGTGGCTCCAGTTCCGGAAC AGTAAACCCTGTTCCGACTACTGCCTC ACCCATATCGTC | SEQ ID NO: 90 |
| DQ683578.1 Hepatitis B virus from South Korea, complete genome | probe_HBV_012017_183 | AATCTTCTCGAGGACTGGGGACCCTGC ACCGAACATGGAGAGCACAACATCAG GATTCCTAGGACCCCTGCTCGTGTTAC AGGCGGGGTTTTTCTTGTTGACAAGAA TCCTCACAATACC | SEQ ID NO: 91 |
| DQ683578.1 Hepatitis B virus from South Korea, complete genome | probe_HBV_012017_184 | ACAGAGTCTAGACTCGTGGTGGACTTC TCTCAATTTTCTAGGGGGAGCACCCAC GTGTCCTGGCCAAAATTCGCAGTCCCC AACCTCCAATCACTCACCAACCTCTTG TCCTCCAATTTG | SEQ ID NO: 92 |
| DQ683578.1 Hepatitis B virus from South Korea, complete genome | probe_HBV_012017_185 | TCCTGGCTATCGCTGGATGTGTCTGCG GCGTTTTATCATATTCCTCTTCATCCTG CTGCTATGCCTCATCTTCTTGTTGGTTC TTCTGGACTACCAAGGTATGTTGCCCG TTTGTCCTCT | SEQ ID NO: 93 |
| DQ683578.1 Hepatitis B virus from South Korea, complete genome | probe_HBV_012017_186 | ACTTCCAGGAACATCAACTACCAGCAC GGGACCATGCAAGACCTGCACGATTCC TGCTCAAGGAACCTCTATGTTTCCCTCT TGTTGCTGTACAAAACCTTCGGACGGA AACTGCACTTG | SEQ ID NO: 94 |
| DQ683578.1 Hepatitis B virus from South Korea, complete genome | probe_HBV_012017_187 | TATTCCCATCCCATCATCCTGGGCTTTC GTAAAATTCCTATGGGAGTGGGCCTCA GTCCGTTTCTCCTGGCTCAGTTTACTAG TGCCATTTGTTCAGTGGTTCGCAGGGC TTTCCCCCAC | SEQ ID NO: 95 |
| DQ683578.1 Hepatitis B virus from South Korea, complete genome | probe_HBV_012017_188 | TGTTTGGCTTTCAGTTATATGGATGAT GTGGTATTGGGGGCCAAGTCTGTGCAA CATCTTGAGTCCCTTTTTACCTCTATTA CCAATTTTCTTTTGTCTTTGGGTATACA TTTGAACCCT | SEQ ID NO: 96 |
| DQ683578.1 Hepatitis B virus from South Korea, complete genome | probe_HBV_012017_189 | AATAAAACCAAACGTTGGGGCTACTCC CTTAACTTCATGGGATATGTAATTGGA AGTTGGGGTACTTTACCACAGGAACAT ATTGTATTAAAACTCAAGCAATGTTTT CGGAAATTGCCT | SEQ ID NO: 97 |
| KR184660.1 Hepatitis B virus isolate SS_3_22, complete genome | probe_HBV_012017_19 | ATGTTAATATGGGCCTAAAAATCAGAC AACTATTGTGGTTTCACATTTCCTGTCT TACTTTTGGAAGAGAAACTGTTCTTGA GTATTTGGTGTCTTTTGGAGTGTGGATT CGCACTCCTC | SEQ ID NO: 98 |
| DQ683578.1 Hepatitis B virus from South Korea, complete genome | probe_HBV_012017_190 | GTAAATAGACCTATTGATTGGAAAGTA TGTCAAAGAATTGTGGGTCTTTTGGAC TTTGCTGCCCCTTTTACACAATGTGGCT ATCCTGCATTGATGCCTTTATATGCAT GTATACAAGCT | SEQ ID NO: 99 |

TABLE 2-continued

| TargetID | ProbeID | Sequence | SEQ ID NO |
|---|---|---|---|
| DQ683578.1 Hepatitis B virus from South Korea, complete genome | probe_HBV_012017_191 | AAGCAGGCTTTCACTTTCTCGCCAACT TACAAGGCCTTTCTGTGTCAACAATAC CTGCACCTTTACCCCGTTGCCCGGCAA CGGTCAGGTCTCTGCCAAGTGTTTGCT GACGCAACCCCC | SEQ ID NO: 100 |
| DQ683578.1 Hepatitis B virus from South Korea, complete genome | probe_HBV_012017_192 | ACTGGATGGGGCTTGGCCATAGGCCAT CGGCGCATGCGTGGAACCTTTGTGGCT CCTCTGCCGATCCATACTGCGGAACTC CTAGCGGCTTGTTTTGCTCGCAGCCGG TCTGGAGCAAAA | SEQ ID NO: 101 |
| DQ683578.1 Hepatitis B virus from South Korea, complete genome | probe_HBV_012017_193 | CTTATCGGGACCGACAACTCTGTTGTC CTCTCTCGGAAATACACCTCCTTCCCA TGGCTGCTCGGGTGTGCTGCCAACTGG ATCCTGCGCGGGACGTCCTTTGTCTAC GTCCCGTCGGCG | SEQ ID NO: 102 |
| DQ683578.1 Hepatitis B virus from South Korea, complete genome | probe_HBV_012017_194 | CTGAATCCCGCGGACGACCCGTCTCGG GGCCGTTTGGGCCTCTATCGTCCCCTTC TTCATCTGCCGTTCCAGCCGACCACGG GGCGCACCTCTCTTTACGCGGTCTCCC CGTCTGTGCCT | SEQ ID NO: 103 |
| DQ683578.1 Hepatitis B virus from South Korea, complete genome | probe_HBV_012017_195 | TCTCATCTGCCGGACCGTGTGCACTTC GCTTCACCTCTGCACGTCGCATGGAAA CCACCGTGAACGCCCATCAGGTCTTGC CCAAGCTCTTACATAAGAGGACTCTTG GACTCTCAGCAA | SEQ ID NO: 104 |
| DQ683578.1 Hepatitis B virus from South Korea, complete genome | probe_HBV_012017_196 | TGTCAACGACCGACCTTGAGGCTTACT TCAAAGACTGTTTGTTTAAAGACTGGG AGGAGTTGGGGGAGGAGACTAGGTTA AAGGTCTTTGTACTAGGAGGCTGTAGG CATAAATTGGTCT | SEQ ID NO: 105 |
| DQ683578.1 Hepatitis B virus from South Korea, complete genome | probe_HBV_012017_197 | GTTCACCAGCACCATGCAACTTTTTCA CCTCTGCCTAATCATCTCATGTTCATGT CCTACTGTTCAAGCCTCCAAGCTGTGC CTTGGGTGGCTTTGGGGCATGGACATT GACCCGTATAA | SEQ ID NO: 106 |
| DQ683578.1 Hepatitis B virus from South Korea, complete genome | probe_HBV_012017_198 | AGAATTTGGAGCTTCTGCGGAGTTACT CTCTTTTTTGCCTTCTGACTTCTTTCCTT CTATTCGAGATCTCCTCGACACCGCCT CTGCTCTATATCGGGAGGCCTTAGAGT CTCCGGAACA | SEQ ID NO: 107 |
| DQ683578.1 Hepatitis B virus from South Korea, complete genome | probe_HBV_012017_199 | TTGTTCACCTCACCATACAGCACTCAG GCAAGCTATTCTGTGTTGGGGTGAGTT GATGAATCTGGCCACCTGGGTGGGAA GTAATTTGGAAGACCCAGCATCCAGGG AATTAGTAGTCAG | SEQ ID NO: 108 |
| KR184660.1 Hepatitis B virus isolate SS_3_22, complete genome | probe_HBV_012017_2 | AATCTTCTCGAGGACTGGGGACCCTGC ACCGAACATGGAGAGCACAACATCAG GATTCCTAGGACCCCTGCTCGTGTTAC AGGCGGGGTTTTCTTGTTGACAAGAA TCCTCACAATACC | SEQ ID NO: 109 |
| KR184660.1 Hepatitis B virus isolate SS_3_22, complete genome | probe_HBV_012017_20 | CCGCTTACAGACCACCAAATGCCCCTA TCTTATCAACACTTCCGGAAACTACTG TTGTTAGACGACGAGGCAGGTCCCCTA GAAGAAGAACTCCCTCGCCTCGCAGAC GAAGGTCTCAAT | SEQ ID NO: 110 |
| DQ683578.1 Hepatitis B virus from South Korea, complete genome | probe_HBV_012017_200 | CTATGTCAATGTTAATATGGGCCTAAA AATCAGACAACTATTGTGGTTTCACAT TTCCTGTCTTACTTTTGGAAGAGAAAC TGTTCTTGAGTATTTGGTGTCTTTTGGA GTGTGGATTCG | SEQ ID NO: 111 |
| DQ683578.1 Hepatitis B virus from South Korea, complete genome | probe_HBV_012017_201 | CACTCCTCCCGCTTACAGACCACCAAA TGCCCCTATCTTATCAACACTTCCGGA AACTACTGTTGTTAGACGACGAGGCAG GTCCCCTAGAAGAAGAACTCCCTCGCC TCGCAGACGAAG | SEQ ID NO: 112 |

TABLE 2-continued

| TargetID | ProbeID | Sequence | SEQ ID NO |
|---|---|---|---|
| DQ683578.1 Hepatitis B virus from South Korea, complete genome | probe_HBV_012017_202 | GTCTCAATCGCCGCGTCGCAGAAGATCTCAATCTCGGGAATCTCAATGTTAGTATCCCTTGGACTCATAAGGTGGGAAACTTTACTGGGCTTTATTCTTCTACTGTACCTGTCTCTAATC | SEQ ID NO: 113 |
| DQ683578.1 Hepatitis B virus from South Korea, complete genome | probe_HBV_012017_203 | CTGAGTGGCAAACTCCCTCCTTTCCTAACATTCATTTACAGGAGGACGTTATTAATAGATGTCAACAATATGTGGGCCCTCTTACAGTTAATGAAAAAAGGAGATTAAAATTAATTATGC | SEQ ID NO: 114 |
| DQ683578.1 Hepatitis B virus from South Korea, complete genome | probe_HBV_012017_204 | CTGCTAGGTTCTATCCTAACCTTACCAAATATTTGCCCTTGGATAAAGGCATTAAACCTTATTATCCTGAACATGCAGTTAATCATTACTTCAAAACTAGGCATTATTTACATACTCTGT | SEQ ID NO: 115 |
| DQ683578.1 Hepatitis B virus from South Korea, complete genome | probe_HBV_012017_205 | GGAAGGCTGGCATTCTATATAAAAGAGAAACTACACGCAGCGCTTCATTTTGTGGGTCACCATATTCTTGGGAACAAGAGCTACAGCATGGGAGGTTGGTCTTCCAAACCTCGACAAGGC | SEQ ID NO: 116 |
| DQ683578.1 Hepatitis B virus from South Korea, complete genome | probe_HBV_012017_206 | ATGGGGACGAATCTTTCTGTTCCCAATCCTCTGGGATTCTTTCCCGATCACCAGTTGGACCCTGCGTTCAGAGCCAACTCAAACAATCCAGATTGGGACTTCAACCCCAACAAGGATCAC | SEQ ID NO: 117 |
| DQ683578.1 Hepatitis B virus from South Korea, complete genome | probe_HBV_012017_207 | TGGCCAGAGGCAAATCAGGTAGGAGCGGGAGCATTCGGGCCAGGGTTCACCCCACCACACGGCGGTCTTTTGGGGTGGAGCCCTCAGGCTCAGGGCATATTGACAACTGTGCCAGCAGCG | SEQ ID NO: 118 |
| KR184660.1 Hepatitis B virus isolate SS_3_22, complete genome | probe_HBV_012017_208 | CATATTGACAACAGTGCCAGCAGCGCCTCCTCCTGCCTCCACCAATCGGCAGTCAGGAAGACAGCCTACTCCCATCTCTCCACCTCTAAGAGACAGTCATCCTCAGGCCATGCAGTGGAA | SEQ ID NO: 119 |
| JN315779.1 Hepatitis B virus genotype C2, complete genome | probe_HBV_012017_209 | CATATTGACAACAGTGCCCGCAGCGCCTCCTCCTGCCTCCACCAATCGGCAGTTAGGAAGACAGCCTACTCCCATCTCTCCACCTCTAAGAGACAGTCATCCTCAGGCCATGCAGTGGAA | SEQ ID NO: 120 |
| KR184660.1 Hepatitis B virus isolate SS_3_22, complete genome | probe_HBV_012017_21 | CGCCGCGTCGCAGAAGATCTCAATCTCGGGAATCTCAATGTTAGTATCCCTTGGACTCATAAGGTGGGAAACTTTACTGGGCTTTATTCTTCTACTGTACCTGTCTTTAATCCTGAGTGG | SEQ ID NO: 121 |
| GQ872211.1 Hepatitis B virus, complete genome | probe_HBV_012017_210 | CATATTGACAACAGTGCCAGCAGCGCCTCCTCCTGCCTCCACCAATCGGCAGTCAGGAAGACAGCCTACTCCCATCTCTCCACCTCTAAGAGACAGTCATCCTCAGGCCATGCAGTGGAA | SEQ ID NO: 122 |
| D23680.1 Hepatitis B virus (B4-HBVST1) complete genome sequence | probe_HBV_012017_211 | CATATTGACAACCGTGCCAGTAGCACCTCCTCCTGCCTCCACCAATCGGCAGTCAGGAAGACAGCCTACTCCCATCTCTCCACCTCTAAGAGACAGTCATCCTCAGGCCATGCAGTGGAA | SEQ ID NO: 123 |
| AY641559.1 Hepatitis B virus isolate He53, complete genome | probe_HBV_012017_212 | CATAGTGACACCAGTGCCAGCAGCGCCTCCTCCTGCCTCCACCAATCGGCAGTCAGGAAGACAGCCTACTCCCATCTCTCCACCTCTAAGAGACAGTCATCCTCAGGCCATGCAGTGGAA | SEQ ID NO: 124 |
| isolate 36Y18HCC","AB014395.1 Hepatitis B virus genomic DNA, complete sequence | probe_HBV_012017_213 | GCATTCGGGCCAGGGTTCACCCCACCACACGGCGGTCTTTTGGGGTGGAGCCCTCAGGCTCAGGGTGCATTGACAACAGTGCCAGTAGCACCTCCTCCTGCCTCCACCAATCGGCAGCCT | SEQ ID NO: 125 |

TABLE 2-continued

| TargetID | ProbeID | Sequence | SEQ ID NO |
|---|---|---|---|
| isolate 22Y04HCC","AB01438 1.1 Hepatitis B virus genomic DNA, complete sequence | probe_HBV_ 012017_214 | CACATTGACAACAGTGCCAGTAGCACC TCCTCCTGCCTCCACCAATCGGCAGTC AGGAAGACAGCCTACTCCCATCTCTCC ACCTCTAAGAGACAGTCATCCTCAGGC CATGCAGTGGAA | SEQ ID NO: 126 |
| DQ683578.1 Hepatitis B virus from South Korea, complete genome | probe_HBV_ 012017_215 | CATATTGACAACTGTGCCAGCAGCGCC TCCTCCTGCCTCCACCAATCGGCAGTC AGAAAGACAGCCTACTCCCATCTCTCC ACCTCTAAGAGACAGTCATCCTCAGGC CATGCAGTGGAA | SEQ ID NO: 127 |
| KR184660.1 Hepatitis B virus isolate SS_3_22, complete genome | probe_HBV_ 012017_22 | CAAACTCCCTCCTTTCCTAACATTCATT TACAGGAAGACATTATTAATAGATGTC AACAATATGTGGGCCCTCTTACAGTTA ATGAAAAAGGAGATTAAAATTAATT ATGCCTGCTAGG | SEQ ID NO: 128 |
| KR184660.1 Hepatitis B virus isolate SS_3_22, complete genome | probe_HBV_ 012017_23 | TTCTATCCTAACCTTACCAAATATTTGC CCTTGGATAAAGGCATTAAACCTTATT ATCCTGAACATGCAGTTAATCATTACT TCAAAACTAGGCATTATTTACATACTC TGTGGAAGGCT | SEQ ID NO: 129 |
| KR184660.1 Hepatitis B virus isolate SS_3_22, complete genome | probe_HBV_ 012017_24 | GGCATTCTATATAAAAGAGAAACTACA CGCAGCGCTTCATTTTGTGGGTCACCA TATTCTTGGGAACAAGAGCTACAGCAT GGGAGGTTGGTCTTCCAAACCTCGACA AGGCATGGGAC | SEQ ID NO: 130 |
| KR184660.1 Hepatitis B virus isolate SS_3_22, complete genome | probe_HBV_ 012017_25 | GAATCTTTCTGTTCCCAATCCTCTGGG ATTCTTTCCCGATCACCAGTTGGACCC TGCGTTCGGAGCCAACTCAAACAATCC AGATTGGGACTTCAACCCCAACAAGG ATCACTGGCCAGA | SEQ ID NO: 131 |
| KR184660.1 Hepatitis B virus isolate SS_3_22, complete genome | probe_HBV_ 012017_26 | GGCAAATCAGGTAGGAGCGGGAGCAT TCGGGCCAGGGTTCACCCCACCACACG GCGGTCTTTTGGGGTGGAGCCCTCAGG CTCAGGGCATATTGACAACAGTGCCAG CAGCGCCTCCTCC | SEQ ID NO: 132 |
| JN315779.1 Hepatitis B virus genotype C2, complete genome | probe_HBV_ 012017_27 | CTCCACAACATTCCACCAAGCTCTGCT AGATCCCAGAGTGAGGGGCCTATATTT TCCTGCTGGTGGCTCCAGTTCCGGAAC AGTAAACCCTGTTCCGACTACTGCCTC ACCCATATCGTC | SEQ ID NO: 133 |
| JN315779.1 Hepatitis B virus genotype C2, complete genome | probe_HBV_ 012017_28 | AATCTTCTCGAGGACTGGGGACCCTGC ACCGAACATGGAGAACACAACATCAG GATTCCTAGGACCCCTGCTCGTGTTAC AGGCGGGGTTTTTCTTGTTGACAAGAA TCCTCACAATACC | SEQ ID NO: 134 |
| JN315779.1 Hepatitis B virus genotype C2, complete genome | probe_HBV_ 012017_29 | ACAGAGTCTAGACTCGTGGTGGACTTC TCTCAATTTTCTAGGGGAAGCACCCAC GTGTCCTGGCCAAAATTCGCAGTCCCC AACCTCCAATCACTCACCAACCTCTTG TCCTCCAATTTG | SEQ ID NO: 135 |
| KR184660.1 Hepatitis B virus isolate SS_3_22, complete genome | probe_HBV_ 012017_3 | ACAGAGTCTAGACTCGTGGTGGACTTC TCTCAATTTTCTAGGGGAGCACCCAC GTGTCCTGGCCAAAATTCGCAGTCCCC AACCTCCAATCACTCACCAACCTCTTG TCCTCCAATTTG | SEQ ID NO: 136 |
| JN315779.1 Hepatitis B virus genotype C2, complete genome | probe_HBV_ 012017_30 | TCCTGGCTATCGCTGGATGTGTCTGCG GCGTTTTATCATATTCCTCTTCATCCTG CTGCTATGCCTCATCTTCTTGTTGGTTC TTCTGGACTACCAAGGTATGTTGCCCG TTTGTCCTCT | SEQ ID NO: 137 |
| JN315779.1 Hepatitis B virus genotype C2, complete genome | probe_HBV_ 012017_31 | ACTTCCAGGAACATCAACTACCAGCAC GGGACCATGCAAGACCTGCACGATTCC TGCTCAAGGAACCTCTATGTTTCCCTCT TGTTGCTGTACAAAACCTTCGGACGGA AACTGCACTTG | SEQ ID NO: 138 |

TABLE 2-continued

| TargetID | ProbeID | Sequence | SEQ ID NO |
|---|---|---|---|
| JN315779.1 Hepatitis B virus genotype C2, complete genome | probe_HBV_012017_32 | TATTCCCATCCCATCATCCTGGGCTTTC GCAAAATTCCTATGGGAGTGGGCCTCA GTCCGTTTCTCCTGGCTCAGTTTACTAG TGCCATTTGTTCAGTGGTTCGCAGGGC TTTCCCCCAC | SEQ ID NO: 139 |
| JN315779.1 Hepatitis B virus genotype C2, complete genome | probe_HBV_012017_33 | TGTTTGGCTTTCAGTTATATGGATGAT GTGGTATTGGGGGCCAAGTCTGTACAA CATCTTGAGTCCCTTTTTACCTCTATTA CCAATTTTCTTTTGTCTTTGGGTATACA TTTGAACCCT | SEQ ID NO: 140 |
| JN315779.1 Hepatitis B virus genotype C2, complete genome | probe_HBV_012017_34 | AATAAAACCAAACGTTGGGGCTACTCC CTTAACTTCATGGGATATGTAATTGGA AGTTGGGGTACTTTACCACAGGAACAT ATTGTACTAAAAATCAAGCAATGTTTT CGGAAACTGCCT | SEQ ID NO: 141 |
| JN315779.1 Hepatitis B virus genotype C2, complete genome | probe_HBV_012017_35 | GTAAATAGACCTATTGATTGGAAAGTA TGTCAAGAATTGTGGGTCTTTTGGGC TTTGCTGCCCCTTTTACACAATGTGGCT ATCCTGCCTTGATGCCTTTATATGCATG TATACAATCT | SEQ ID NO: 142 |
| JN315779.1 Hepatitis B virus genotype C2, complete genome | probe_HBV_012017_36 | AAGCAGGCTTTCACTTTCTCGCCAACT TACAAGGCCTTTCTGTGTAAACAATAT CTGCACCTTTACCCCGTTGCCCGGCAA CGGTCAGGTCTCTGCCAAGTGTTTGCT GACGCAACCCCC | SEQ ID NO: 143 |
| JN315779.1 Hepatitis B virus genotype C2, complete genome | probe_HBV_012017_38 | CTTATCGGGACTGACAACTCTGTTGTC CTCTCTCAGAAATACACCTCCTTCCCA TGGCTGCTCGGGTGTGCTGCCAACTGG ATCCTGCGCGGGACGTCCTTTGTCTAC GTCCCGTCGGCG | SEQ ID NO: 144 |
| KR184660.1 Hepatitis B virus isolate SS_3_22, complete genome | probe_HBV_012017_4 | TCCTGGCTATCGCTGGATGTGTCTGCG GCGTTTTATCATATTCCTCTTCATCCTG CTGCTATGCCTCATCTTCTTGTTGGTTC TTCTGGACTACCAAGGTATGTTGCCCG TTTGTCCTCT | SEQ ID NO: 145 |
| JN315779.1 Hepatitis B virus genotype C2, complete genome | probe_HBV_012017_40 | TCTCATCTGCCGGTCCGTGTGCACTTC GCTTCACCTCTGCACGTCGCATGGAGA CCACCGTGAACGCCCACCAGGTCTTGC CCAAGGTCTTACATAAGAGGACTCTTG GACTCTCAGCAA | SEQ ID NO: 146 |
| JN315779.1 Hepatitis B virus genotype C2, complete genome | probe_HBV_012017_41 | TGTCAACAACCGACCTTGAGGCATACT TCAAAGACTGTTTGTTTAAAGACTGGG AGGAGTTGGGGGAGGAGATTAGGTTA AAGGTCTTTGTACTAGGAGGCTGTAGG CATAAAATTGGTCT | SEQ ID NO: 147 |
| JN315779.1 Hepatitis B virus genotype C2, complete genome | probe_HBV_012017_42 | GTTCACCAGCACCATGCAACTTTTTCA CCTCTGCCTAATCATCTCATGTTCATGT CCTACTGTTCAAGCCTCCAAGCTGTGC CTTGGGTGGCTTTGGGGCATGGACATT GACCCGTATAA | SEQ ID NO: 148 |
| JN315779.1 Hepatitis B virus genotype C2, complete genome | probe_HBV_012017_43 | AGAATTTGGAGCTTCTGTGGAGTTACT CTCTTTTTTGCCTTCTGACTTCTTTCCTT CTATTCGAGATCTCCTCGACACCGCCT CTGCTCTGTATCGGGAGGCCTTAGAGT CTCCGGAACA | SEQ ID NO: 149 |
| JN315779.1 Hepatitis B virus genotype C2, complete genome | probe_HBV_012017_44 | TTGTTCACCTCACCATACAGCACTCAG GCAAGCTATTCTGTGTTGGGGTGAGTT ATTGAATCTGGCCACCTGGGTGGGAAG TAATTTGGAAGACCCAGCATCCAGGGA ATTAGTAGTCAG | SEQ ID NO: 150 |
| JN315779.1 Hepatitis B virus genotype C2, complete genome | probe_HBV_012017_45 | CTATGTCAATGTTAATATGGGCCTAAA AATCAGACAACTATTGTGGTTTCACAT TTCCTGTCTTACTTTTGGAAGAGAAAC TGTTCTTGAGTATTTGGTGTCTTTTGGA GTGTGGATTCG | SEQ ID NO: 151 |

TABLE 2-continued

| TargetID | ProbeID | Sequence | SEQ ID NO |
|---|---|---|---|
| JN315779.1 Hepatitis B virus genotype C2, complete genome | probe_HBV_012017_47 | GTCTCAATCGCCGCGTCGCCGAAGATC TCAATCTCGGGAATCTCAATGTTAGTA TCCCTTGGACTCATAAGGTGGGAAACT TTACTGGGCTTTATTCTTCTACTGTACC TGTCTTTAATC | SEQ ID NO: 152 |
| JN315779.1 Hepatitis B virus genotype C2, complete genome | probe_HBV_012017_48 | CTGAGTGGCAAACTCCCTCCTTTCCTA ACATTCATTTACAGGAGGACATTATTA ATAGATGTCAACAATATGTGGGCCCTC TCACAGTTAATGAAAAAAGGAGATTA AAATTAATTATGC | SEQ ID NO: 153 |
| KR184660.1 Hepatitis B virus isolate SS_3_22, complete genome | probe_HBV_012017_5 | ACTTCCAGGAACATCAACTACCAGCAC GGGACCATGCAAGACCTGCACGATTCC TGCTCAAGGAACCTCTATGTTTCCCTCT TGTTGCTGTACAAAACCTTCGGACGGA AACTGCACTTG | SEQ ID NO: 154 |
| JN315779.1 Hepatitis B virus genotype C2, complete genome | probe_HBV_012017_51 | ATGGGGACGAATCTTTCTGTTCCCAAT CCTCTGGGATTCTTTCCCGATCACCAG TTGGACCCTGCGTTCGGAGCCAACTCA AACAATCCAGATTGGGACTTCAACCCC AACAAGGATCAC | SEQ ID NO: 155 |
| JN315779.1 Hepatitis B virus genotype C2, complete genome | probe_HBV_012017_52 | TGGCCAGAGGCAAATCAGGTAGGAGC GGGAGCATTCGGGCAGGGTTCACCCC ACCACACGGCGGTCTTTTGGGGTGGAG CCCTCAGGCTCAGGGCATATTGACAAC AGTGCCCGCAGCG | SEQ ID NO: 156 |
| GQ872211.1 Hepatitis B virus, complete genome | probe_HBV_012017_53 | CTCCACAACATTCCACCAAGCTCTGCT AGATCCCAGAGTGAGGGGCCTATATTT TCCTGCTGGTGGCTCCAGTTCCGGAAC AGTAAACCCTGTTCCGACTACTGCCTC ACCCATATCGTC | SEQ ID NO: 157 |
| GQ872211.1 Hepatitis B virus, complete genome | probe_HBV_012017_54 | AATCTTCTCGAGGACTGGGGACCCTGC ACCGAACATGGAGAGCACAACATCAG GATTCCTAGGACCCCTGCTCGTGTTAC AGGCGGGGTTTTCTTGTTGACAAGAA TCCTCACAATACC | SEQ ID NO: 158 |
| GQ872211.1 Hepatitis B virus, complete genome | probe_HBV_012017_55 | ACAGAGTCTAGACTCGTGGTGGACTTC TCTCAATTTTCTAGGGGGAGCACCCAC GTGTCCTGGCCAAAATTCGCAGTCCCC AACCTCCAATCACTCACCAACCTCTTG TCCTCCAATTTG | SEQ ID NO: 159 |
| GQ872211.1 Hepatitis B virus, complete genome | probe_HBV_012017_56 | TCCTGGCTATCGCTGGATGTGTCTGCG GCGTTTTATCATATTCCTCTTCATCCTG CTGCTATGCCTCACCTTCTTGTTGGTCC TTCTGGACTACCAAGGTATGTTGCCCG TTTGTCCTCT | SEQ ID NO: 160 |
| GQ872211.1 Hepatitis B virus, complete genome | probe_HBV_012017_57 | ACTTCCAGGAACATCAACTACCAGCAC GGGACCATGCAAGACCTGCACGACTCC TGCTCAAGGAACCTCTATGTTTCCCTCT TGTTGCTGTACAAAACCTTCGGACGGA AACTGCACTTG | SEQ ID NO: 161 |
| GQ872211.1 Hepatitis B virus, complete genome | probe_HBV_012017_58 | TATTCCCATCCCATCATCCTGGGCTTTC GCAAGATTCCTATGGGAGTGGGCCTCA GTCCGTTTCTCCTGGCTCAGTTTACTAG TGCCATTTGTTCAGTGGTTCGCAGGGC TTTCCCCCAC | SEQ ID NO: 162 |
| GQ872211.1 Hepatitis B virus, complete genome | probe_HBV_012017_59 | TGTTTGGCTTTCAGTTATATGGATGAT GGGGTATTGGGGGCCAAGTCTGTACAA CATCTTGAGTCCCTTTTTACCTCTATTA CCAATTTTCTTTTGTCTTTGGGTATACA TTTGAACCCT | SEQ ID NO: 163 |
| KR184660.1 Hepatitis B virus isolate SS_3_22, complete genome | probe_HBV_012017_6 | TATTCCCATCCCATCATCCTGGGCTTTC GCAAGATTCCTATGGGAGTGGGCCTCA GTCCGTTTCTCCTGGCTCAGTTTACTAG TGCCATTTGTTCAGTGGTTCGTAGGGC TTTCCCCCAC | SEQ ID NO: 164 |

TABLE 2-continued

| TargetID | ProbeID | Sequence | SEQ ID NO |
|---|---|---|---|
| GQ872211.1 Hepatitis B virus, complete genome | probe_HBV_012017_60 | AATAAAACCAAACGTTGGGGCTACTCC CTTAACTTCATGGGATATGTAATTGGA AGTTGGGGTACTTTACCACAGGAACAT ATTGTATTAAAAATCAAGAAATGTTTT CGGAAACTGCCT | SEQ ID NO: 165 |
| GQ872211.1 Hepatitis B virus, complete genome | probe_HBV_012017_61 | GTAAATAGACCTATTGATTGGAAAGTA TGTCAAAGAATTGTGGGTCTTTTGGGC TTTGCTGCCCCTTTTACACAATGTGGCT ATCCTGCCTTAATGCCTTTATATGCATG TATACAATCT | SEQ ID NO: 166 |
| GQ872211.1 Hepatitis B virus, complete genome | probe_HBV_012017_62 | AAGCAGGCTTTCACTTTCTCGCCCACT TACAAGGCCTTTCTGTGTCAACAATAC CTGCACCTTTACCCCGTTGCCCGGCAA CGGTCAGGTCTCTGCCAAGTGTTTGCT GACGCAACCCCC | SEQ ID NO: 167 |
| GQ872211.1 Hepatitis B virus, complete genome | probe_HBV_012017_63 | ACTGGATGGGGCTTGGCCATAGGCCAT CGGCGCATGCGTGGAACCTTTGTGGCT CCTCTGCCGATCCATACTGCGGAACTC CTAGCAGCTTGTTTTGCTCGCAGCCGG TCTGGAGCAAAA | SEQ ID NO: 168 |
| GQ872211.1 Hepatitis B virus, complete genome | probe_HBV_012017_64 | CTTATCGGGACTGACAACTCTGTTGTC CTCTCTCGGAAATACACCTCCTTCCCA TGGCTGCTCGGATGTGCTGCCAACTGG ATCCTGCGCGGGACGTCCTTTGTCTAC GTCCCGTCGGCG | SEQ ID NO: 169 |
| GQ872211.1 Hepatitis B virus, complete genome | probe_HBV_012017_65 | CTGAATCCCGCGGACGACCCGTCTCGG GGCCGTTTGGGCCTCTACCGTCCCCTT CTTCATCTGCCGTTCCAGCCGACCACG GGGCGCACCTCTCTTTACGCGGTCTCC CCGTCTGTGCCT | SEQ ID NO: 170 |
| GQ872211.1 Hepatitis B virus, complete genome | probe_HBV_012017_66 | TCTCATCTGCCGGTCCGTGTGCACTTC GCTTCACCTCTGCACGTCGCATGGAAA CCACCGTGAACGCCCACCAGGTCTTGC CCAAGGTCTTATATAAGAGGACTCTTG GACTCTCAGCAA | SEQ ID NO: 171 |
| GQ872211.1 Hepatitis B virus, complete genome | probe_HBV_012017_67 | TGTCAACGACCGACCTTGAGGCATACT TCAAAGACTGTTTGTTTAAAGACTGGG AGGAGTTGGGGGAGGAGATTAGGTTA ATGATCTTTGTACTAGGAGGCTGTAGG CATAAATTGGTCT | SEQ ID NO: 172 |
| GQ872211.1 Hepatitis B virus, complete genome | probe_HBV_012017_68 | GTTCACCAGCACCATGCAACTTTTTCA CCTCTGCCTAATCATCTCATGTTCATGT CCTACTGTTCAAGCCTCCAAGCTGTGC CTTGGGTGGCTTTGGGGCATGGACATT GACCCGTATAA | SEQ ID NO: 173 |
| GQ872211.1 Hepatitis B virus, complete genome | probe_HBV_012017_69 | AGAATTTGGAGCTTCTGCGGAGTTACT CTCTTTTTTGCCTTCTGACTTCTTTCCG TCTATTCGAGATCTCCTCGACACCGCC TCTGCTCTGTATAGGGAGGCCTTAGAG TCTCCGGAACA | SEQ ID NO: 174 |
| KR184660.1 Hepatitis B virus isolate SS_3_22, complete genome | probe_HBV_012017_7 | TGTTTGGCTTTCAGTTATATGGATGAT GTGGTATTGGGGGCCAAGTCTGTACAA CATCTTGAGTCCCTTTTTACCTCTATTA CCAATTTTCTTGTGTCTTTGGGTATACA TTTGAACCCT | SEQ ID NO: 175 |
| GQ872211.1 Hepatitis B virus, complete genome | probe_HBV_012017_70 | TTGTTCACCTCACCATACAGCACTCAG GCAAGCTATTCTGTGTTGGGGTGAGTT GATGAATCTGGCCACCTGGGTGGGAA GTAATTGGAAGACCCAGCATCCAGGG AATTAGTAGTCGG | SEQ ID NO: 176 |
| GQ872211.1 Hepatitis B virus, complete genome | probe_HBV_012017_71 | CTATGTCAATGTTAATATGGGCCTAAA ACTCAGACAACTATTGTGGTTTCACAT TTCCTGTCTTACTTTTGGAAGAGAAAC TGTTCTTGAGTATTTGGTGTCTTTTGGA GTGTGGATTCG | SEQ ID NO: 177 |

TABLE 2-continued

| TargetID | ProbeID | Sequence | SEQ ID NO |
|---|---|---|---|
| GQ872211.1 Hepatitis B virus, complete genome | probe_HBV_012017_72 | CACTCCTACCGCTTACAGACCACCAAA TGCCCCTATCTTATCAACACTTCCGGA AACTACTGTTGTTAGACGACGAGGCAG GTCCCCTAGAAGAAGAACTCCCTCGCC TCGCAGACGAAG | SEQ ID NO: 178 |
| GQ872211.1 Hepatitis B virus, complete genome | probe_HBV_012017_73 | GTCTCAATCGCCGCGTCGCAGAAGATC TCAATCTCGGGAATCTCAATGTTAGTA TCCCTTGGACTCATAAGGTGGGAAACT TTACTGGGCTTTATTCTTCTACTGTACC TGTCTTTAATC | SEQ ID NO: 179 |
| GQ872211.1 Hepatitis B virus, complete genome | probe_HBV_012017_74 | CTGAGTGGCAAACTCCCTCCTTTCCTA ACATTCATTTACAGGAGGACATTATTA ATAGATGTCAACAATATGTGGGCCCTC TTACAGTTAATGAAAAAAGGAGATTA AAATTAATTATGC | SEQ ID NO: 180 |
| GQ872211.1 Hepatitis B virus, complete genome | probe_HBV_012017_75 | CTGCTAGGTTCTATCCTAACCTTACCA AATATTTGCCCTTGGATAAGGGCATTA AACCTTATTATCCTGAACATGCAGTTA ATCATTACTTCAAAACTAGGCATTATT TACATACTCTGT | SEQ ID NO: 181 |
| GQ872211.1 Hepatitis B virus, complete genome | probe_HBV_012017_76 | GGAAGGCTGGCATTCTATATAAAAGA GAAACTACACGCAGCGCTTCATTTTGT GGGTCACCATATTCTTGGGAACAAGAG CTACAGCATGGGAGGTTGGTCTTCCAA ACCTCGAAAAGGC | SEQ ID NO: 182 |
| GQ872211.1 Hepatitis B virus, complete genome | probe_HBV_012017_77 | ATGGGGACGAATCTTTCTGTTCCCAAT CCTCTGGGATTCTTTCCCGATCACCAG TTGGACCCTGCATTCGGAGCCAACTCA AACAATCCAGATTGGGACTTCAACCCC AACAAGGATCAC | SEQ ID NO: 183 |
| GQ872211.1 Hepatitis B virus, complete genome | probe_HBV_012017_78 | TGGCCAGAGGCAACTCAGGTAGGAGC GGGAGCATTCGGGCCAGGGTTCACCCC ACCACACGGCGGTCTTTTGGGGTGGAG CCCTCAGGCTCAGGGCATATTGACAAC AGTGCCAGCAGCG | SEQ ID NO: 184 |
| D23680.1 Hepatitis B virus (B4-HBVST1) complete genome sequence | probe_HBV_012017_79 | CTCCACAACATTCCACCAAGCTCTGCT AGACCCCAGGTGAGGGGCCTATACTT TCCTGCTGGTGGCTCCAGTTCCGGAAC AGTAAACCCTGTTCCGACTACTGCCTC ACCCATATCGTC | SEQ ID NO: 185 |
| KR184660.1 Hepatitis B virus isolate SS_3_22, complete genome | probe_HBV_012017_8 | AATAAAACCAAACGTTGGGGCTACTCC CTTAACTTCATGGGATATGTAATTGGA AGTTGGGGTACTTTACCACAGGAACAT ATTGTACAAAAACTCAAGCAATGTTTT CGGAAACTGCCT | SEQ ID NO: 186 |
| D23680.1 Hepatitis B virus (B4-HBVST1) complete genome sequence | probe_HBV_012017_80 | AATCTTCTCGAGGACTGGGGACCCTGC ACCGAACATGGAGAACACAACATCAG GATTCCTAGGACCCCTGCTCGTGTTAC AGGCGGGGTTTTTCTTGTTGACAAGAA TCCTCACAATACC | SEQ ID NO: 187 |
| D23680.1 Hepatitis B virus (B4-HBVST1) complete genome sequence | probe_HBV_012017_81 | ACAGAGTCTAGACTCGTGGTGGACTTC TCTCAATTTTCTAGGGGGAGCACCCAC GTGTCCTGGCCAAAATTCGCAGTCCCC AACCTCCAATCACTCACCAACCTCTTG TCCTCCAATTTG | SEQ ID NO: 188 |
| D23680.1 Hepatitis B virus (B4-HBVST1) complete genome sequence | probe_HBV_012017_82 | ACCTGGCTATCGCTGGATGTGTCTGCG GCGTTTTATCATATTCCTCTTCATCCTG CTGCTATGCCTCATCTTCTTGTTGGTTC TTCTGGACTACCAAGGTATGTTGCCCG TTTGTCCTCT | SEQ ID NO: 189 |
| D23680.1 Hepatitis B virus (B4-HBVST1) complete genome sequence | probe_HBV_012017_83 | ACTTCCAGGAACATCAACTACCAGCAC AGGACCATGCAAGACCTGCACGATTCC TGCTCAAGGAACCTCTATGTTTCCCTCT TGTTGCTGTACAAAACCTTCGGACGGA AACTGCACTTG | SEQ ID NO: 190 |

TABLE 2-continued

| TargetID | ProbeID | Sequence | SEQ ID NO |
|---|---|---|---|
| D23680.1 Hepatitis B virus (B4-HBVST1) complete genome sequence | probe_HBV_012017_84 | TATTCCCATCCCATCATCCTGGGCTTTC GCAAGATTCCTATGGGAGTGGGCCTCA GTCCGTTTCTCCTGGCTCAGTTTACTAG TGCCATTTGTTCAGTGGTTCGTAGGGC TTTCCCCCAC | SEQ ID NO: 191 |
| D23680.1 Hepatitis B virus (B4-HBVST1) complete genome sequence | probe_HBV_012017_85 | TGTTTGGCTTTCAGTTATATGGATGAT GTGGTATTGGGGGCCAAGTCTGTACAA CATCTTGAGTCCCTTTTTACCTCTATTA CCCATTTTCTTTTATCTTTGGGTATACA TTTGAACCCC | SEQ ID NO: 192 |
| D23680.1 Hepatitis B virus (B4-HBVST1) complete genome sequence | probe_HBV_012017_86 | AATAAAACCAAACGTTGGGGCTACTCC CTTAACTTCATGGGATATGTAATTGGA TGTTGGGGTACTTTACCGCAAGAACAT ATTGTACTAAAAATCAAGCAATGTTTT CGAAAACTGCCT | SEQ ID NO: 193 |
| D23680.1 Hepatitis B virus (B4-HBVST1) complete genome sequence | probe_HBV_012017_87 | GTAAATAGACCTATTGATTGGAAAGTA TGTCAGAGAATTGTGGGTCTTTTGGGC TTTGCTGCCCCTTTTACACAATGTGGCT ATCCTGCCTTAAAGCCTTTATATGCAT GTATACAAGCT | SEQ ID NO: 194 |
| D23680.1 Hepatitis B virus (B4-HBVST1) complete genome sequence | probe_HBV_012017_88 | AAGCAGGCTTTCACTTTCTCGCCGACT TACAAGGCCTTTCTGTGTAAACAATAT CTGAACCTTTACCCCGTTGCCCGGCAA CGGTCAGGTCTCTGCCAAGTGTTTGCT GACGCAACCCCC | SEQ ID NO: 195 |
| D23680.1 Hepatitis B virus (B4-HBVST1) complete genome sequence | probe_HBV_012017_89 | ACTGGCTGGGGCTTGGCTATCGGCCAT CGCCGCATGCGTGGAACCTTTGTGGCT CCTCTGCCGATCCATACTGCGGAACTC CTAGCAGCTTGTTTTGCTCGCAGCCGG TCTGGAGCGAAA | SEQ ID NO: 196 |
| KR184660.1 Hepatitis B virus isolate SS_3_22, complete genome | probeHBV_012017_9 | GTAAATAGACCTATTGACTGGAAAGTA TGTCAAAGAATTGTGGGTCTTTTGGGC TTTGCTGCCCCTTTTACACAATGTGGCT ATCCTGCCTTGATGCCTTTATATGCATG TATACAAGCT | SEQ ID NO: 197 |
| D23680.1 Hepatitis B virus (B4-HBVST1) complete genome sequence | probe_HBV_012017_90 | CTTATCGGCACCGACAACTCTGTTGTC CTCTCTCGGAAATACACCTCATTTCCA TGGCTGCTAGGGTGTGCTGCCAACTGG ATCCTGCGCGGGACGTCCTTTGTCTAC GTCCCGTCGGCG | SEQ ID NO: 198 |
| D23680.1 Hepatitis B virus (B4-HBVST1) complete genome sequence | probe_HBV_012017_91 | CTGAATCCCGCGGACGACCCGTCTCGG GGCCGTTTGGGACTCTACCGTCCCCTT CTTCATCTGCCGTTCCGGCCAACCACG GGGCGCACCTCTCTTTACGCGGTCTCC CCGTCTGTGCCT | SEQ ID NO: 199 |
| D23680.1 Hepatitis B virus (B4-HBVST1) complete genome sequence | probe_HBV_012017_92 | TCTCATCTGCCGGGCCGTGTGCACTTC GCTTCACCTCTGCACGTCGCATGGAAA CCTCCGTGAACGCCCACCAGGTCTTGC CCAAGGTCTTATATAAGAGGACTCTTG GACTCTCAGCGA | SEQ ID NO: 200 |
| D23680.1 Hepatitis B virus (B4-HBVST1) complete genome sequence | probe_HBV_012017_93 | TGTCAACGACCGACCTTGAGGCATACT TCAAAGACTGTTTGTTTAAGGACTGGG AGGAGTTGGGGGAGGTACTAGGAGGC TGTAGGCATAAATTGGTCTGTTCACCA GCACCATGCAACT | SEQ ID NO: 201 |
| D23680.1 Hepatitis B virus (B4-HBVST1) complete genome sequence | probe_HBV_012017_94 | TTTTCACCTCTGCCTAATCATCTCATGT TCATGTCCTACTGTTCAAGCCTCCAAG CTGTGCCTTGGGTGGCTTTGGGGCATG GACATTGACCCGTATAAAGAATTTGGA GCTTCTGTGGA | SEQ ID NO: 202 |
| D23680.1 Hepatitis B virus (B4-HBVST1) complete genome sequence | probe_HBV_012017_95 | GTTACTCTCTTTTTTGCCTTCTGACTTC TTTCCTTCTATTCGAGATCTCCTCGACA CCGCCTCAGCTCTGTATCGGGAGGCCT TAGAGTCTCCGGAACATTGTTCTCCTC ACCATACAGC | SEQ ID NO: 203 |

TABLE 2-continued

| TargetID | ProbeID | Sequence | SEQ ID NO |
|---|---|---|---|
| D23680.1 Hepatitis B virus (B4-HBVST1) complete genome sequence | probe_HBV_012017_96 | ACTCAGGCAAGCTATTCTGTGTTGGGG TGAGTTGATGAATCTGGCCACCTGGGT GGGAAGTAATTTGGAAGACCCAGCAT CCAGGGAATTAGTAGTCAGCTATGTCA ATGTTAATATGGG | SEQ ID NO: 204 |
| D23680.1 Hepatitis B virus (B4-HBVST1) complete genome sequence | probe_HBV_012017_97 | CCTAAAAATCAGACAACTACTGTGGTT TCACATTTCCTGTCTTACTTTTGGAAGA GAAACTGTTCTTGAGTATTTGGTGTCTT TTGGAGTGTGGATTCGCACTCCTCCTG CTTACAGACC | SEQ ID NO: 205 |
| D23680.1 Hepatitis B virus (B4-HBVST1) complete genome sequence | probe_HBV_012017_98 | ACCAAATGCCCCTATCTTATCAACACT TCCGGAAACTACTGTTGTTAGACGACG AGGCAGGTCCCCTAGAAGAAGAACTC CCTCGCCTCGCAGACGAAGGTCTCAAT CGCCGCGTCGCAG | SEQ ID NO: 206 |
| D23680.1 Hepatitis B virus (B4-HBVST1) complete genome sequence | probe_HBV_012017_99 | AAGATCTCAATCTCGGGAATCTCAATG TTAGTATCCCTTGGACTCATAAGGTGG GAAACTTTACTGGGCTTTATTCTTCTAC TGTACCTGTCTTTAATCCTGAGTGGCA AACTCCCTCCT | SEQ ID NO: 207 |
| isolate 36Y18HCC","AB01439 5.1 Hepatitis B virus genomic DNA, complete sequence | probe_HBV_012017_a_1 | CACCAAGCTCTGATAGACCCCAGAGTA AGGGGCCTATACTTTCCTGCTGGTGGC TCCAGTTCCGGAACAGTAAACCCTGTT CCGACTACTGCCTCACCCATATCGTCA ATCTTCTCGAGG | SEQ ID NO: 208 |
| isolate 36Y18HCC","AB01439 5.1 Hepatitis B virus genomic DNA, complete sequence | probe_HBV_012017_a_2 | CTTTCTCGCCAACTTACAAGGCCTTTCT GTGTAAACAATATCTGAACCTTTACCC CGTTGCTCGGCAACGGTCAGGTTTATG CCAAGTGTTTGCTGACGCAACCCCCAC TGGATGGGGCT | SEQ ID NO: 209 |
| isolate 22Y04HCC","AB01438 1.1 Hepatitis B virus genomic DNA, complete sequence | probe_HBV_012017_a_3 | GGAAGGCAGGCATTCTATATAAGAGA GAAACTACACGCAGCGCCTCATTTTGT GGGTCACCATATTCTTGGGAACAAGAG CTACAGCATGGGAGGTTGGTCTTCCAA ACCTCGACAAGGC | SEQ ID NO: 210 |
| JN315779.1 Hepatitis B virus genotype C2, complete genome | probe_HBV_012017_a_4 | ACTGGATGGGCTTGGCCATAGGCCAT CAGCGCATGCGTGGAACCTTTGTGGCT CCTCTGCCGATCCATACTGCGGAACTC ATAGAAGCTTGTTTTGCTCGCAGCCGG TCTGGAGCGAAA | SEQ ID NO: 211 |
| JN315779.1 Hepatitis B virus genotype C2, complete genome | probe_HBV_012017_a_5 | CTGAATCCCGCGGACGACCCGTCTCGG GACCGTTTGGGCCTCTACCGTCCCCTT CTTCATCTGCCGTTCCGGCCGACCACG GGGCGCACCTCTCTTTACGCGGTCTCC CCGTCTGTGCCT | SEQ ID NO: 212 |
| JN315779.1 Hepatitis B virus genotype C2, complete genome | probe_HBV_012017_a_6 | CACTCCTACCGCTTACAGACCACCAAA TGCCCCTATCTTATCAACACTTCCGGA AACTACTGTTGTTAGACGACGAGGCAG GTCCCCTAGAAGAAGAACTCCCTCGCC TCGCAGACGAAG | SEQ ID NO: 213 |
| JN315779.1 Hepatitis B virus genotype C2, complete genome | probe_HBV_012017_a_7 | CTGCTAGGTTCTATCCTAACCATACCA AATATTTGCCCTTGGATAAAGGCATTA AACCTTATTATCCTGAACATGTAGTTA ATCATTACTTCAAAACTAGGCATTATT TACATACTTTGG | SEQ ID NO: 214 |
| JN315779.1 Hepatitis B virus genotype C2, complete genome | probe_HBV_012017_a_8 | GGAAGGCTGGCATTCGGTATAAGAGA GAAACTACACGCAGCGCCTCATTTTGT GGGTCACCATATTCTTGGGAACAAGAG CTACAGCATGGGAGGTTGGTCTTCCAA ACCTCGACAAGGC | SEQ ID NO: 215 |

Example 2: Next-Generation Sequencing Analysis for Detection of HBV Insertion Site 2-1. DNA shearing
1) Extract genomic DNA from liver tissue of a patient with hepatitis and crush (sonication) it into nucleotides of about 100 to 120 base pairs in length. After diluting 1 µg of gDNA passed through Quality Control (QC) on a 96-well plate with 60 µL, transfer it to a Covaris strip tube and seal with sealing tape.
2) Transfer the strip tube to a steel rack and mount it on a device.
3) As Table 3 below, shear it after setting Covaris (Covaris LE200).

TABLE 3

| | |
|---|---|
| Duty Factor | 30 |
| PIP, W | 400 |
| Cycles per Burst | 200 |
| Time (seconds) | 100 |
| Temperature | 5 to 9° C. |

2) Sample purification
1) Transfer the sheared sample into a new 1.5 mL tube.
2) Place 90 µL of AMPure beads, vortex it for 5 seconds, and perform incubation at room temperature for 5 minutes.
3) Place the sample in a magnetic particle concentrator (MPC), and after 3 minutes, discard the supernatant.
4) Add 200 µL of 70% ethanol while the sample is in MPC, and after 1 minute, discard the supernatant (repeat twice).
5) Completely dry the beads (5 minutes to 10 minutes).
6) Remove the sample tube from MPC, add 50 µL of nuclease-free water, and resuspend AMPure beads.
7) After incubating at room temperature for 2 minutes to 3 minutes, spin it down.
8) Place the sample in MPC, and after 2 minutes, transfer 48 µL of the supernatant into a new 1.5 mL tube.

2-3. Repairing the ends
1) After mixing all of the components of Table 4 below, lid off in PCR and perform at 20° C. for 30 minutes.

TABLE 4

| Component | Volume |
|---|---|
| DNA sample | 48 µL |
| Water | 35.2 µL |
| End repair buffer | 10 µL |
| dNTP mix | 1.6 µL |
| T4 DNA polymerase | 1 µL |
| Klenow DNA polymerase | 2 µL |
| T4 PNK | 2.2 µL |
| Total | 100 µL |

2) Sample purification
Place the sample performed in 3. 1) above into a new 1.5 mL tube.
Place 180 µL of AMPure beads (1.8X), vortex it for 5 seconds, and perform incubation for 5 minutes at room temperature.
Place the sample in a magnetic particle concentrator (MPC), and after 3 minutes, discard the supernatant.
While the sample is in MPC, add 200 µL of 70% ethanol, and after 1 minute, discard the supernatant (repeat twice).
Completely dry the beads (5 minutes to 10 minutes).
Remove the sample tube from MPC, add 32 µL of nuclease-free water, and resuspend AMPure beads.
After incubating for 2 minutes to 3 minutes at room temperature, spin it down.
Place the sample in MPC, and after 2 minutes, transfer 30 µL of the supernatant into a new 1.5 mL tube.

2-4. Addition of A' base to the 3' end of DNA fragment
1) After adding all of the components of Table 5 below, lid off in PCR and perform at 37° C. for 30 minutes.

TABLE 5

| Component | Volume |
|---|---|
| DNA sample | 30 µL |
| Water | 11 µL |
| 10X Klenow DNA polymerase buffer | 5 µL |
| dATP | 1 µL |
| Klenow exo(3' to 5' exo minus) | 3 µL |
| Total | 50 µL |

2) Sample purification
Place the sample performed in 4. 1) above into a new 1.5 mL tube.
Place 180 µL of AMPure beads (1.8X), vortex it for 5 seconds, and perform incubation for 5 minutes at room temperature.
Place the sample in a magnetic particle concentrator (MPC), and after 3 minutes, discard the supernatant.
While the sample is in MPC, add 200 µL of 70% ethanol, and after 1 minute, discard the supernatant (repeat twice).
Completely dry the beads (5 minutes to 10 minutes).
Remove the sample tube from MPC, add 15 µL of nuclease-free water, and resuspend AMPure beads.
After incubating for 2 minutes to 3 minutes at room temperature, spin it down.
Place the sample in MPC, and after 2 minutes, transfer 13 µL of the supernatant into a new 1.5 mL tube.

2-5. Adapter ligation to DNA fragment
1) After adding all of the components of Table 6 below, lid off in PCR and perform at 20° C. for 15 minutes.

TABLE 6

| Component | Volume |
|---|---|
| DNA sample | 13 µL |
| Water | 15.5 µL |
| 5X T4 DNA ligase buffer | 10 µL |
| Adapter oligo mix | 10 µL |
| T4 DNA ligase | 1.5 µL |
| Total | 50 µL |

2) Sample purification
Place the sample performed in 2-5. 1) above into a new 1.5 mL tube.
Place 180 µL of AMPure beads (1.8X), vortex it for 5 seconds, and perform incubation for 5 minutes at room temperature.
Place the sample in a magnetic particle concentrator (MPC), and after 3 minutes, discard the supernatant.
While the sample is in MPC, add 200 µL of 70% ethanol, and after 1 minute, discard the supernatant (repeat twice).
Completely dry the beads (5 minutes to 10 minutes).

Remove the sample tube from MPC, add 17 μL of nuclease-free water, and resuspend AMPure beads.
After incubating for 2 minutes to 3 minutes at room temperature, spin it down.
Place the sample in MPC, and after 2 minutes, transfer 15 μL of the supernatant into a new 1.5 mL tube.

2-6. Amplification of adapter-ligated library
1) Prepare components in Table 7 below.

TABLE 7

| Component | Volume |
| --- | --- |
| Index Adapter-ligated library | 15 μL |
| Water | 21 μL |
| SureSelect primer 1.0 (Forward) | 1.25 μL |
| SureSelect Indexing Pre-Capture PCR(Reverse) Primer | 1.25 μL |
| Herculase 5X Reaction Buffer | 10 μL |
| dNTP mix | 0.5 μL |
| Herculase II polymerase | 1 μL |
| Total | 50 μL |

2) Amplify according to the Pre-LM PCR program below.

TABLE 8

| Step | PCR step | Time |
| --- | --- | --- |
| Step 1. | 98° C. | 2 mins |
| Step 2. | 98° C. | 30 s |
| Step 3. | 65° C. | 30 s |
| Step 4. | 72° C. | 1 min |
| Step 5. | Repeat Steps 2 to 4 for 6 times | |
| Step 6. | 72° C. | 10 minutes |
| Step 7. | 4° C. | Hold |

2-7. Sample purification
Transfer the sample passed through the steps above into a new 1.5 mL tube.
Place 180 μL of AMPure beads (1.8X), vortex it for 5 seconds, and perform incubation for 5 minutes at room temperature.
Place the sample in a magnetic particle concentrator (MPC), and after 3 minutes, discard the supernatant.
While the sample is in MPC, add 200 μL of 70% ethanol, and after 1 minute, discard the supernatant (repeat twice).
Completely dry the beads (5 minutes to 10 minutes).
Remove the sample tube from MPC, add 17 μL of nuclease-free water, and resuspend AMPure beads.
After incubating for 2 minutes to 3 minutes at room temperature, spin it down.
Place the sample in MPC, and after 2 minutes, transfer 15 μL of the supernatant into a new 1.5 mL tube.

Figure 2:
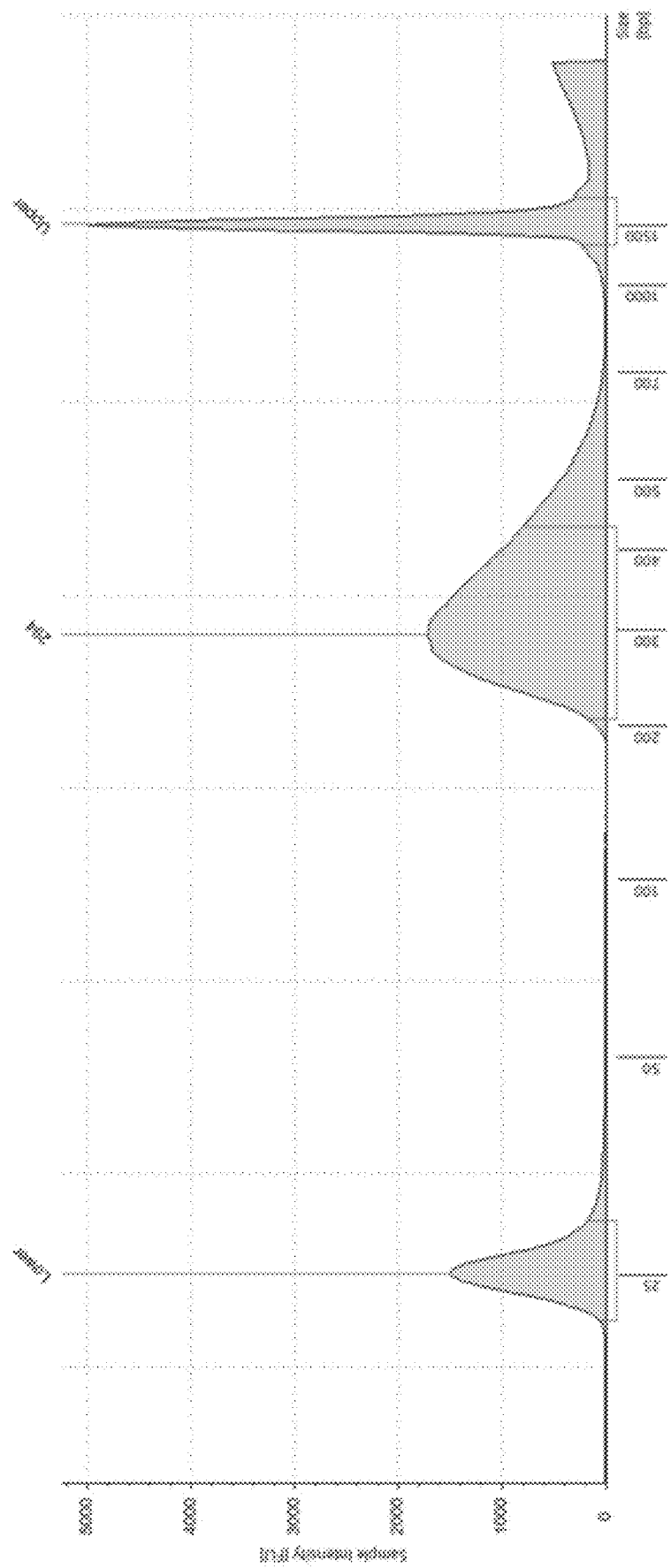
FIG. 2 and FIG. 3 show results of measuring between libraries using Agilent 4200 Tape Station and D1000 Screen Tape.

2-8. Assessment of quality and quantity
In order to confirm whether the library size was made within the intended range to optimize the efficiency of hybridization and to confirm the concentration to check if the amount at which hybridization could be attempted was achieved, the size and concentration of a library were measured using Agilent 4200 Tape Station and D1000 Screen Tape, and the result was shown in FIG. 2. As shown in FIG. 2, peaks having a DNA library size of about 250 bp to 350 bp were mostly observed.

2-9. Hybridization
1) Drill a hole in a 1.5 mL tube lid and dispense 200 ng or more and 500 ng or less of the prepped library.
2) Completely dry using SpeedVac (45° C.) (60 minutes).

3) After making a block mix as below, place 5.6 μL each into a dried tube, vortex lightly, and resuspend the library (prepped library).

TABLE 9

| Component | Volume |
| --- | --- |
| Pre-LM sample 500 ng | 3.4 μL |
| SureSelect Block #1 (green cap) | 2.5 μL |
| SureSelect Block #2 (blue cap) | 2.5 μL |
| SureSelect Block #3 (brown cap) | 0.6 μL |
| Total | 9 μL |

4) After making a hybridization buffer with the composition of Table 10 below, dispense 0.2 mL into a PCR tube.

TABLE 10

| Component | Volume |
| --- | --- |
| SureSelect Hyb #1 | 6.63 μL |
| SureSelect Hyb #2 (red) | 0.27 μL |
| SureSelect Hyb #3 (yellow) | 2.65 μL |
| SureSelect Hyb #4 | 3.45 μL |
| Total | 13 μL |

5) Perform RNase block dilution as Table 11 below.

TABLE 11

| Capture Library Size | RNase Block dilution |
| --- | --- |
| 3.0 Mb or more | 25% (1:3) |
| 3.0 Mb or less | 10% (1:9) |

6-1) The volume used for hybridization is different depending on the total size of a probe. It is because the concentration of the probe itself is different. Since the volume is different, the dilution ratio and the used volume of the RNase block should be different. The final concentration of RNase block is the same as 6-1 and 6-2. As a result, in the case of a general bait of 3 MB or more, it is applied to a large-sized probe targeting the entire exome.

TABLE 12

| Component | Volume |
| --- | --- |
| Hybridization Buffer mixture from step 4 | 13 μL |
| 25% RNase Block solution from step 5-1, 5-2 | 2 μL |
| Capture Library 3 Mb | 5 μL |
| Total | 20 μL |

6-2) The volume used for hybridization is different depending on the total size of a probe. It is because the concentration of the probe itself is different. Since the volume is different, the dilution ratio and the used volume of the RNase block should be different. The final concentration of RNase block is the same as 6-1 and 6-2. In the case of a general bait of 3 MB or less, it was applied in this experiment.

TABLE 13

| Component | Volume |
| --- | --- |
| Hybridization Buffer mixture from step 4 | 13 μL |
| 10% RNase Block solution from step 5-1, 5-2 | 5 μL |
| Capture Library 3 Mb | 2 μL |
| Total | 20 μL |

7) For gDNA library+block mix plate or a strip tube (prepped library), set up the PCR program as below and perform.

TABLE 14

| PCR program | Time |
| --- | --- |
| Lid temperature: 105° C. | |
| 95° C. | 5 minutes |
| 65° C. | Hold |

8) When the temperature of a prepped library (an entire set of libraries made available for NGS sequencing of gDNA samples used in the experiment) sample reaches 65° C., place the prepped library sample in a capture library (a set of probes including a target area of the size of 120 nt) and a hybridization mix (a reagent (buffer) to enable hybridization conditions) prepared above, and mix well by pipetting up and down for 3 to 5 times.
9) Close the lid well and hybridize for 24 hours at 65° C. (lid 105° C.) (up to 72 hours is possible).

2-10. Preparation of magnetic beads
1) Preheat SureSelect Wash Buffer #2 in a water bath (65° C.).
2) Vortex well Dynal MyOne Streptavidin T1 (Invitrogen) magnetic beads.
3) Dispense 50 μL per sample into a 1.5 mL tube.
4) Wash the beads as the following.
 a. Place 200 μL of SureSelect Binding buffer and vortex lightly.
 b. After spinning down, place it in DynaMag-2 device for 1 minute, and remove the supernatant.
 c. Repeat the above process for a total of 3 times.
5) Resuspend the beads washed in 200 μL of SureSelect Binding buffer.

2-11. Hybridization capture selection with SureSelect
1) After mixing a hybridization mixture and a bead solution, mount it on a rotator and perform a reaction at room temperature for 30 minutes (check if the sample in the tube is mixed well).
2) After spinning down, place it in DynaMag-2 device for 3 minutes and remove the supernatant.
3) Place 200 μL of SureSelect Wash Buffer #1 and vortex until the beads are completely resuspended.
4) Incubate at room temperature for 15 minutes. Lightly vortex every 5 minutes to mix the beads well.
5) After spinning down, place it in DynaMag-2 device for 3 minutes and remove the supernatant.
6) Wash the beads as the following.
 a. Place 200 μL of prewarmed SureSelect Wash Buffer #2 and vortex until the beads are completely resuspended.
 b. Incubate at 65° C. for 10 minutes. Lightly vortex every 5 minutes to mix the beads well.
 c. After spinning down, place it in DynaMag-2 device and remove the supernatant.
 d. Repeat the above process for a total of 3 times.
7) Place 30 μL of nuclease-free water in MPC and resuspend.

2-12. Addition of index tags by amplification after hybridization (post-hybridization)
1) Prepare reagents as in Table 15 below.

TABLE 15

| Reagent | Volume |
| --- | --- |
| Captured DNA | 30 μL |
| Water | 6.5 μL |
| Herculase 5X Reaction Buffer | 10 μL |
| dNTP mix (25 mM each) | 0.5 μL |
| Herculase II DNA polymersase | 1 μL |
| SureSelect Indexing Post-Capture PCR (Forward) Primer | 1 μL |
| Index PCR (reverse) primer | 1 μL |
| Total | 50 μL |

2) Perform amplification according to the PCR program below.

TABLE 16

| Step | PCR step | Time |
| --- | --- | --- |
| Step 1. | 98° C. | 1 min |
| Step 2. | 98° C. | 20 s |
| Step 3. | 57° C. | 1 min |
| Step 4. | 72° C. | 1 min |
| Step 5. | Repeat steps 2 to 4 for 11 times | |
| Step 6. | 72° C. | 10 minutes |
| Step 7. | 4° C. | Hold |

2-13. Purification of sample using Agencourt AMPure XP beads
1) Vortex 50 μL of the amplified DNA library and 90 μL of AMPure beads (1.8X) and mix.
2) Incubate at room temperature for 5 minutes.
3) Place the sample in a magnetic particle concentrator (MPC), and after 3 minutes, discard the supernatant.
4) Add 500 μL of 70% ethanol while the sample is in MPC, and after 1 minute, discard the supernatant (repeat twice).
5) Completely dry the beads (5 minutes to 10 minutes).
6) Remove the sample tube from MPC, add 15 μL of nuclease-free water, and resuspend AMPure beads.
7) After incubating at room temperature for 2 minutes to 3 minutes, spin it down. 8) Place the sample in MPC, and after 2 minutes, place 30 μL of the supernatant into a new 1.5 mL tube.

Figure 3:
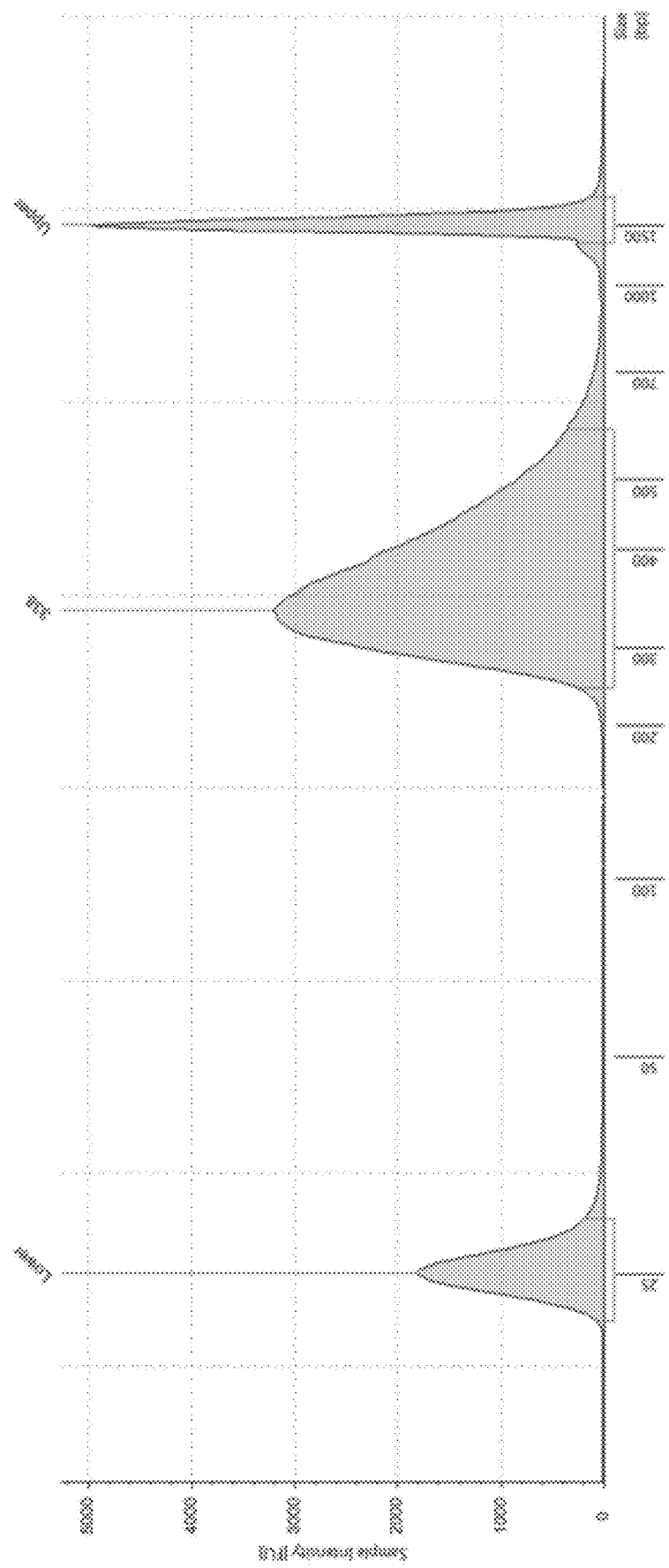

2-14. Confirmation of Library It is a library state after hybridization has been performed and only a target region has been amplified. In FIG. 2, only the target region was selected from the entire library, and the library size was increased by 50 bp at once while adding an index and the like during the amplification process. It is the library at the final stage for sequencing, and in order to finally confirm whether sequencing is possible (determining whether or not a library is made normally), the size and state of the DNA library are confirmed using Agilent 4200 TapeStation and D1000 ScreenTape, and the concentration of the DNA library is confirmed using qPCR. As shown in FIG. 3, the library size has peaks of 250 bp to 350 bp.

Figure 4:
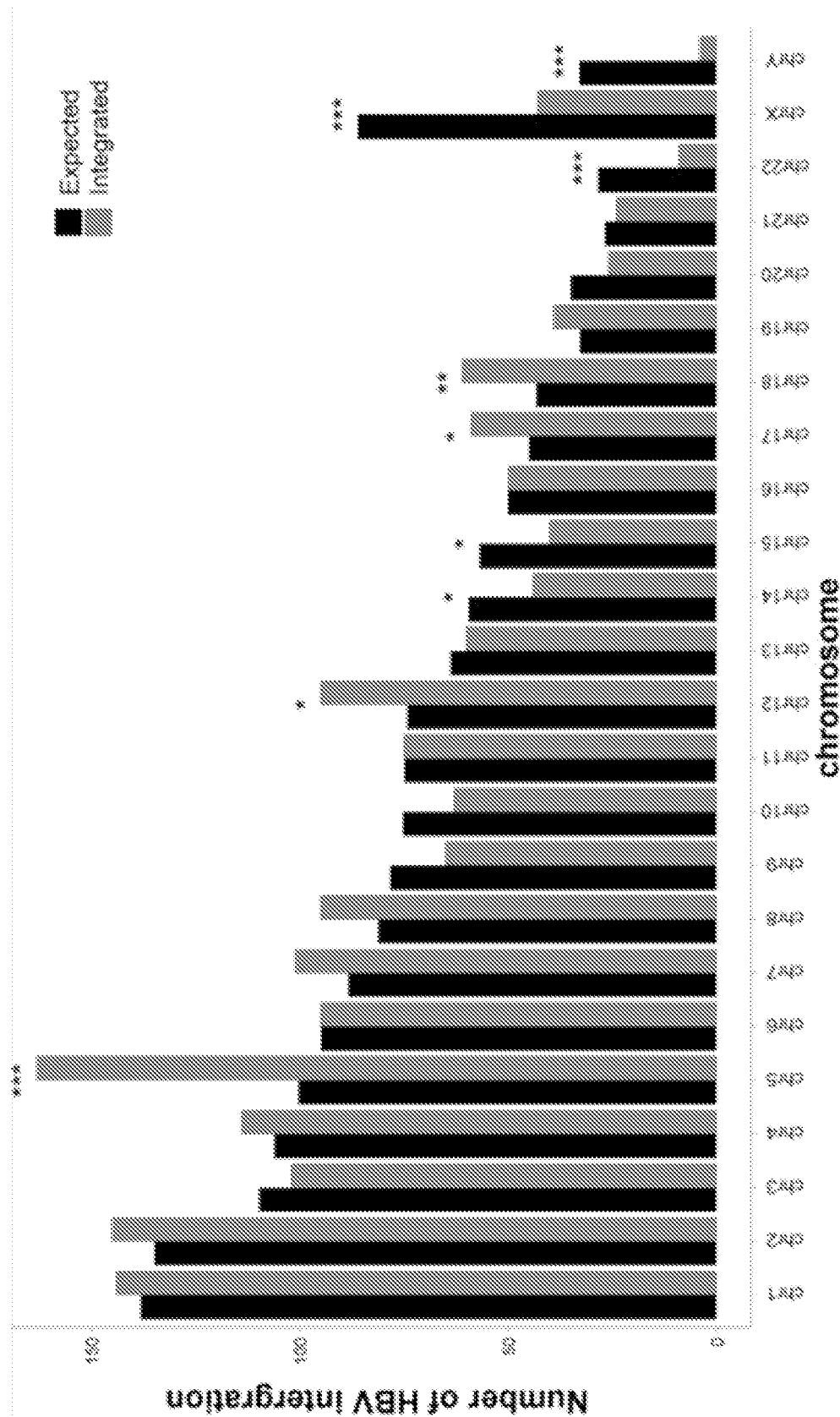
FIG. 4 shows results of breakpoint analysis of human chromosomes in tumor tissue.
Figure 4:
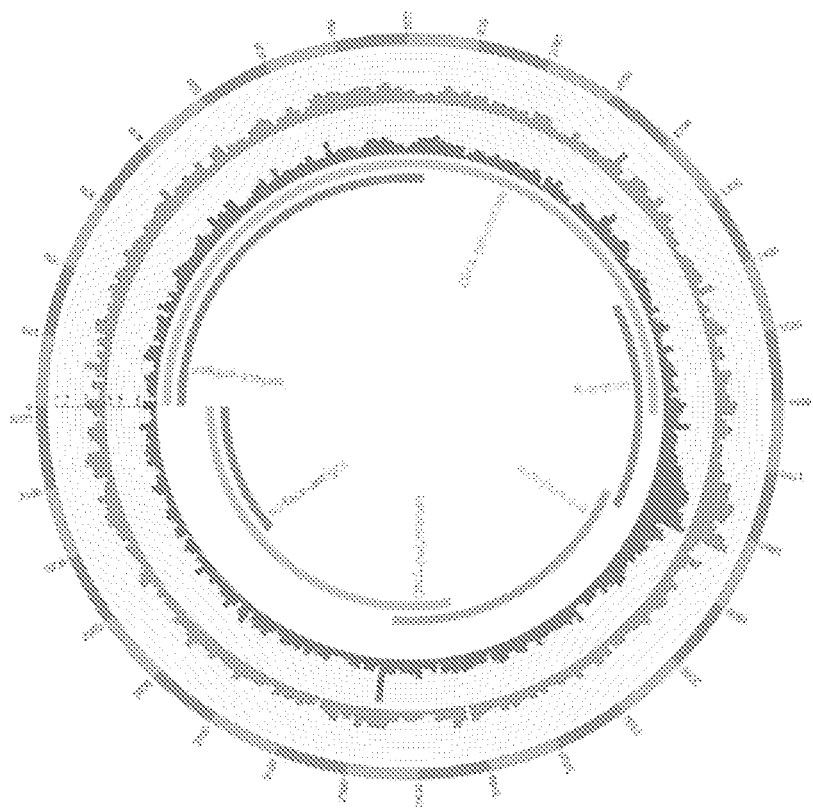
Figure 4:
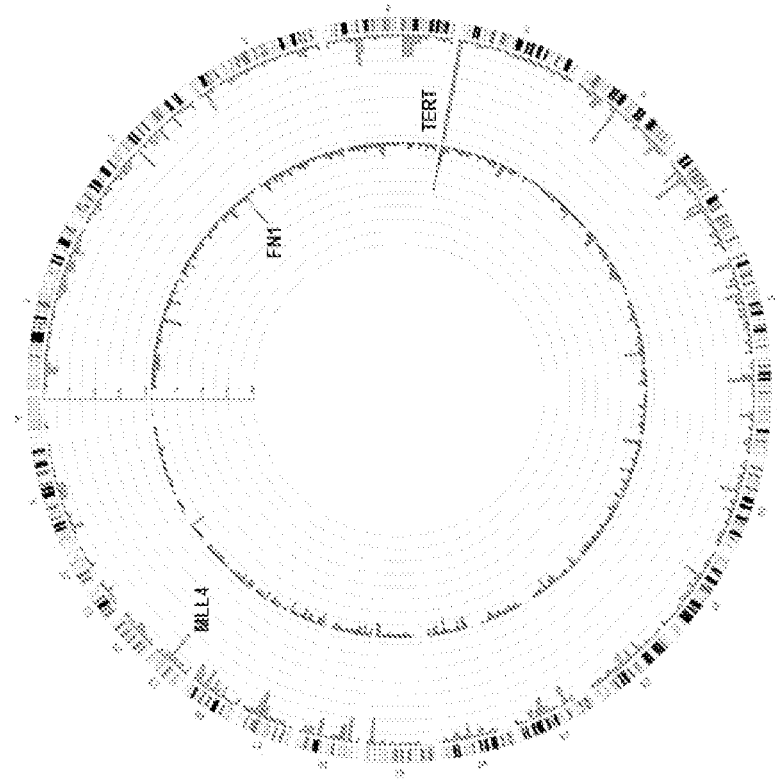

2-15. Analysis of HBV Gene Insertion Site
The sequenced reads were mapped to the reference sequence (HBV+Human genome) to create a BAM file, which is a binary of the Sequence Alignment map (SAM) file. Among the mapped reads, the chimeric read that was split-mapped to HBV and the human genome was selected to identify break points. Next, for each point, a region that satisfied read count >10, average mapping quality (MQ)>20 was defined as an HBV-human integration site, and the location of HBV and the human genome was searched. Recurrently inserted human genes were collected, gene-annotation was performed and analyzed to discover the overall biological function of each gene, and the results were shown in FIG. 4. As shown in FIG. 4, it was found that the HBV virus was inserted into the overall human whole genome, and in particular, it was confirmed that the insertion rate was high in the TERT protomer region of chromosome number 5. Through this, it is possible to comprehensively infer the effect of HBV insertion on the human genome. HBV insertion is an important direct tumor-inducing phenomenon in the occurrence of liver cancer, and understanding of an insight into its biological action is required, but there is little understanding of HBV insertion until now. Meanwhile, the NGS technique has become available to identify non-biased insertion sites therefor, but whole genome sequencing (WGS, full-length genome sequencing) is very difficult to use in clinical practice due to its cost limitations. The present invention described above is a sequencing method that applies the existing NGS technique targeting HBV inserted in the human genome, and since it is a high-depth sequencing analysis that is more efficient than WGS and can detect more HBV insertion sites at a cost of about ⅓ of the WGS method, it is considered that the academic-clinical value thereof will be very high in the future compared to its cost-effectiveness.

What is claimed is:

1. A probe composition for detecting hepatitis B virus (HBV) comprising 215 probes, each probe of the 215 probes comprising a unique nucleotide sequence from other probes of the 215 probes, each unique nucleotide sequence consisting of the nucleotide sequences of SEQ ID NO: 1 to SEQ ID NO: 215 with additional nucleotides of each probe comprising a nucleotide sequence comprising at least one adapter sequence.

2. The probe composition of claim 1, wherein the probe composition is capable of detecting an insertion site of hepatitis B virus in a human genome, wherein the human genome is derived from liver tissue of a patient with hepatitis.

3. The probe composition of claim 1, wherein the probe composition is capable of detecting an insertion site of hepatitis B virus (HBV) using an analysis method of next-generation sequencing.

4. The probe composition of claim 1, wherein the length of each of the 215 probes is greater than 120 base pairs.

5. A kit for detecting hepatitis B virus (HBV), comprising the probe composition of claim 1.

6. A method for detecting hepatitis B virus (HBV) through next-generation sequencing (NGS), the method comprising hybridizing a target sample with the probe composition of claim 1 to capture a target gene.

7. The method of claim 6, wherein the hybridizing is performed at a temperature of 65° C. for 16 hours to 24 hours.

8. A method for detecting hepatitis B virus (HBV), comprising:
(a) hybridizing a target sample comprising a target gene with the probe composition of claim 1 to capture a target gene and amplifying to create a library for next-generation sequencing analysis; and
(b) sequencing the library to confirm an insertion site of hepatitis B virus (HBV) in a human genome.

9. The method of claim 8, wherein the hybridizing is performed at a temperature of 65° C. for 16 hours to 24 hours.

10. A method for providing information for a diagnosis of liver cancer, using the method of claim 8.

* * * * *